United States Patent
Takemori et al.

(10) Patent No.: US 6,323,149 B1
(45) Date of Patent: Nov. 27, 2001

(54) CATALYST COMPONENT AND CATALYST CONTAINING THE COMPONENT FOR POLYMERIZATION OF OLEFINS

(75) Inventors: Toshifumi Takemori, Ichihara; Shigeharu Yamamoto, Yotsukaido; Masatoshi Tsuchitani, Ichihara, all of (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/571,863

(22) Filed: May 16, 2000

Related U.S. Application Data

(60) Division of application No. 09/220,589, filed on Dec. 28, 1998, which is a continuation-in-part of application No. PCT/JP97/04441, filed on Dec. 4, 1997.

(30) Foreign Application Priority Data

Jul. 9, 1997 (JP) .................................................... 9-184199

(51) Int. Cl.$^7$ ........................................................ C08F 4/64

(52) U.S. Cl. ......................... 502/114; 502/103; 502/132; 502/153; 526/160; 526/165; 526/943

(58) Field of Search ................................. 502/103, 114, 502/153, 132; 526/160, 165, 943

(56) References Cited

U.S. PATENT DOCUMENTS

| | | |
|---|---|---|
| 4,752,597 | 6/1988 | Turner . |
| 5,126,303 | 6/1992 | Resconi et al. . |
| 5,643,845 | 7/1997 | Tajima et al. . |
| 5,700,750 | 12/1997 | Tsutsui et al. . |
| 5,780,659 | 7/1998 | Schmid et al. . |
| 5,880,056 | 3/1999 | Tsutsui et al. . |

FOREIGN PATENT DOCUMENTS

| | | |
|---|---|---|
| 0 324 477 A | 7/1989 | (EP) . |
| 58-19309 | 2/1983 | (JP) . |
| 60-35007 | 2/1985 | (JP) . |
| 62-230802 | 10/1987 | (JP) . |
| 2-302410 | 12/1990 | (JP) . |

OTHER PUBLICATIONS

Sun, Qi et al., "Study of highly active titanocene/n–BuLi catalyst system in the hydrogenation of olefin," *Gaodeng Xuexiao Huaxue Xuebao*, vol. 17, No. 9, pp. 1441–1445 (1996) (Abstract).

LeNest, Jean Francois et al., "Ethylene polymerization with new catalysts: Et$_2$AlCl–organotitanium compounds," *Polym. Bull.*, vol. 1, No. 3, 1978, pp. 227–232.

Bourg, Stephane et al., "New Stable Titanocene and Zirconocene Catalyst Precursors for Polysilane Synthesis via Dehydrocoupling of Hydrosilanes," *Organometallics*, vol. 14, No. 1, 1995, pp. 564–566.

(List continued on next page.)

*Primary Examiner*—David W. Wu
*Assistant Examiner*—Caixia Lu
(74) *Attorney, Agent, or Firm*—Oliff & Berridge, PLC

(57) ABSTRACT

The present invention relates to a metallocene compound as a catalyst component for the polymerization of olefins, said compound, is stable to air and moisture so that generates no hydrogen halide by hydrolysis and easily handled, and has a high storage stability and a high catalyst activity. Specifically, the catalyst component for the polymerization of olefins comprises a transition metal composition represented by the general formula [1] and [2]:

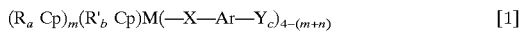

[1]

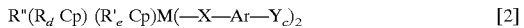

[2]

wherein M is Ti, Zr or Hf; ($R_a$ Cp),($R'_b$ Cp), ($R_d$ Cp) and ($R''_e$ Cp ) each is a radical having the cyclopentadienyl skeleton; R" is a radical which links ($R_d$ Cp) and ($R'_e$ Cp); (—X—Ar—$Y_c$) is a grouping in which the aromatic ring Ar substituted by a specified radical Y bonds to M through an oxygen or sulphur atom X.

8 Claims, 1 Drawing Sheet

OTHER PUBLICATIONS

Koepf, Hartmut et al., "Synthesis and spectroscopic characterization of new bis(thiolato)–and enedithiolato–bis($n^5$–cyclopentadienyl)hafnium(IV) complexes," Anorg. Chem., Org. Chem., vol. 40B, No. 10, 1985, pp. 1338–1343.

Repo, Timo et al., "Phenoxy–substituted zirconocenes in ethylene polymerization," J. Organomet. Chem., vol. 541, No. 1–2, 1997, pp. 363–366.

Habaue, Shigeki et al., "Chiral ethylenebis(4,5,6, 7–tetrahydro–1–indenyl) complexes of zirconium and hafnium: Separation and application to asymmetric polymerization," Macromol. Rapid Commun., vol. 18, No. 8, 1997, pp. 707–713.

CATALYST COMPONENT AND CATALYST CONTAINING THE COMPONENT FOR POLYMERIZATION OF OLEFINS

This application is a divisional of U.S. application Ser. No. 09/220,589 filed on Dec. 28, 1998, which is a continuation on part of PCT/JP97/04441 filed on Dec. 4, 1997.

TECHNICAL FIELD

The present invention relates to a catalyst component for the polymerization of olefins, a polymerization catalyst containing the component and a process for the polymerization of olefins by using the catalyst, and more particularly, to a catalyst component for the polymerization of olefins which is stable to air, moisture and so on and not corrosive to metal, a polymerization catalyst containing said component, having a high polymerization activity and being capable of producing olefin polymers, and a process for the polymerization of olefins.

BACKGROUND ART

Recently, as a catalyst which can homopolymerize ethylene or copolymerize ethylene and α-olefin with a high polymerization activity, there is proposed a new catalyst for the polymerization of olefins comprising a transition metal compound such as metallocene compound of zirconium and an organic aluminum oxy compound. As a process for the homo- or copolymerization of ethylene by using such catalyst, there has been proposed, for example, in Japanese Patent Application Laid-open Nos. Sho 58(1983)-19309, Sho 60(1985)-35007, etc.

In such a prior art, it has been disclosed that as a transition metal compound component, a metallocene compound is available, which has an alkadienyl radical such as a cyclopentadienyl radical, etc, as a ligand for the transition metal, and further an alkyl radical, a halogen atom, etc.

However, the metallocene compound in such prior arts may show a high polymerization activity as a compound having a halogen atom bound directly to the transition metal atom, but need a treatment with alcohol or water after the polymerization depending on the kind of olefins and the process for the polymerization, so that hydrogen halide may be formed disadvantageously which may occur rusts and corrosions in equipments. Further, a metallocene compound having an alkyl radical bound directly to the metal atom has high polymerization activity relatively and does not form. undesirable hydrogen halide, but there are some disadvantages that it is extremely unstable to a little air or moisture, is apt to lower the catalyst activity remarkably by deterioration in the operation or to deteriorate with time in storage, as a result, a special care and equipment to the handling and storage of catalyst component are required. Thus, for example, as seen in Japanese Patent Application Laid-open No. Sho 62(1987)-230802, there has been proposed a process in which the halogen atom or alkyl radical bound to the metal atom is converted to an alkoxy or phenoxy radical to eliminate the formation of hydrogen halide and improve the stability of the metallocene compound. In this case, however, disadvantageously the activity as catalyst for the polymerization of olefins is in general lowered.

Accordingly, it has been strongly desired to develop as a metallocene compound, a transition metal compound, which satisfies at the same time three requirements that it does not contain a halogen atom directly bound to the metal atom, as a result, it does not generate undesirable hydrogen halide, that it is stable to air and moisture so that it may be dealt with easily and has a high storage stability and that it has a high activity on using as a catalyst for the polymerization of olefins. And also it has been strongly desired to provide a process for the polymerization of olefins therewith.

After studying earnestly in view of the present status as mentioned above,: it has been found that a metallocene compound may eliminate the disadvantages as mentioned above which has a radical comprising a cyclopentadienyl skeleton coordinated to the transition metal and in which an aromatic ring substituted with a special substituent is bound through an oxygen or a sulphur to the transition metal, and it shows an excellent activity on using it as a catalyst for the polymerization of olefins resulting in the accomplishment of the present invention.

DISCLOSURE OF INVENTION

Accordingly, the present invention relates at first to a catalyst component for the polymerization of olefins which comprises a transition metal compound represented by the general formula [1] or [2]:

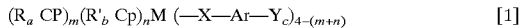

$$(R_a \text{ CP})_m(R'_b \text{ Cp})_n M (-X-Ar-Y_c)_{4-(m+n)} \quad [1]$$

wherein M represents titanium, zirconium or hafnium, Cp represents a radical having the cyclopentadienyl skeleton, R and R' represent a hydrogen atom, an alkyl, an alkenyl, an aryl, an alkylaryl, an arylalkyl or an alkylsilyl radical, X represents an oxygen or a sulphur atom, Ar represents an aromatic ring, Y represents a hydrogen atom, a hydrocarbon radical, a silyl radical, a halogen atom, a halogenated hydrocarbon radical, a nitrogen-containing organic radical, an oxygen-containing organic radical or a sulphur-containing organic radical, each of a and b is an integer of 0 to 5, each of m and n is an integer of 0 to 3 and that m+n is an integer of 1 to 3, and c is an integer of 1 to 5, proviso Y does not represent a hydrogen atom when Ar is a benzene ring;

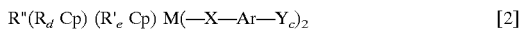

$$R''(R_d \text{ Cp}) (R'_e \text{ Cp}) M(-X-Ar-Y_c)_2 \quad [2]$$

wherein M represents titanium, zirconium or hafnium, Cp represents a radical having the cyclopentadienyl skeleton, R and R' represent a hydrogen atom, an alkyl, an alkenyl, an aryl, an alkylaryl, an arylalkyl or an alkylsilyl radical, R" represents a divalent radical which links $(R_d \text{ Cp})$ and $(R'_e \text{ Cp})$ and is selected from an alkylene, an arylalkylene, a dialkylsilylene, a dialkylgermylene, an alkylphosphindiyl or an alkylimino radical, X represents an oxygen or a sulphur atom, Ar represents an aromatic radical, Y represents a hydrogen atom, a hydrocarbon radical, a silyl radical, a halogen atom, a halogenated hydrocarbon radical, a nitrogen-containing organic radical, an oxygen-containing organic radical or a sulphur-containing organic radical, d and e each represents an integer of 0 to 4, and c is an integer of 1 to 5, proviso that Y is not a hydrogen atom when Ar is a benzene ring.

Secondly, the present invention relates to a catalyst for the polymerization of olefins comprising [A] a transition metal compound represented by the above-mentioned general formula [1] or [2], [B] an organic aluminum oxy compound or a cation generator and occasionally [C] an organic aluminum compound, and thirdly to a: process for the polymerization of olefins characterized by polymerizing or copolymerizing olefins in the presence of said catalyst for the polymerization of olefins.

The metallocene compound as a catalyst component for the polymerization of olefins has as mentioned-above in general a halogen atom or an alkyl radical as the groupings to bond the transition metal and the polymerization activity thereof is remarkably lowered when all groupings are converted to a phenoxy or thiophenoxy radical. However, the present inventors have found unexpected function in which in case a specified substutient is introduced to an aromatic: ring like a phenoxy radical or thiophenoxy radical or the like, a higher polymerization activity is realized without the reduction of activity rather than the metallocene compound to which a halogen atom or an alkyl radical is bound.

The present invention will be illustrated in detail hereinafter, in which the term "polymerizations" means the homopolymerization and copolymerization.

The metallocene catalyst component according to the present invention is a transition metal compound represented by any one of the following two general formulae:

$$(R_a\ CP)_m(R'_b\ Cp)_n M(-X-Ar-Y_c)_{4-(m+n)} \quad [1]$$

wherein M represents titanium, zirconium or hafnium, Cp represents a radical having the cyclopentadienyl skeleton, R and R' represent a hydrogen atom, an alkyl, an alkenyl, an aryl, an alkylaryl, an arylalkyl or an alkylsilyl radical, X represents an oxygen or a sulphur atom, Ar represents an aromatic ring, Y represents a hydrogen atom, a hydrocarbon radical, a silyl radical, a halogen atom, a halogenated hydrocarbon radical, a nitrogen-containing organic radical, an oxygen-containing organic radical or a sulphur-containing radical, each of a and b is an integer of 0 to 5, each of m and n is an integer of 0 to 3 and m+n is an integer of 1 to 3, and c is an integer of 1–5, proviso that Y is not a hydrogen atom when Ar is a benzene ring;

$$R''(R_d\ Cp)(R'_e\ Cp)\ M\ (-X-Ar-Y_c)_2 \quad [2]$$

wherein M represents titanium, zirconium or hafnium, Cp represents a radical having the cyclopentadienyl skeleton, R and R' represent a hydrogen atom, an alkyl, an alkenyl, an aryl, an alkylaryl, an arylalkyl or an alkylsilyl radical, R" represents a divalent radical which links ($R_d$ Cp) and ($R'_e$ Cp) and is selected from an alkylene, an arylalkylene, a dialkylsilylene, a dialkylgermylene, an alkylphosphindiyl, or an alkylimino radical, X represents an oxygen or a sulphur atom, Ar represents an aromatic ring, Y represents a hydrogen atom, a hydrocarbon radical, a silyl radical, a halogen atom, a halogenated hydrocarbon radical, a nitrogen-containing organic radical, an oxygen-containing organic radical or a sulphur-containing organic radical, each of d and e is an integer of 0 to 4, and c is an integer of 1 to 5, proviso that Y is not a hydrogen atom when Ar is a benzene ring.

In the general formulae [1] and [2], the ligand Cp is not critical but may be a grouping having the cyclopentadienyl skeleton and include not only a cyclopentadienyl radical but the cyclopentadienyl radicals in which two vicinal carbon atoms in the cyclopentadienyl ring bond to other carbon atoms to form a 4- or 5- or 6-membered ring. As the cyclopentadienyl radicals in which two vicinal carbon atoms in the cyclopentadienyl ring bond to other carbon atoms to form a 4- or 5- or 6-membered ring, there are mentioned, for example, an indenyl, tetrahydroindenyl, fluorenyl radical, etc.

In the general formulae [1] and [2], R and R' each is preferably, a hydrogen, an alkyl radical having 1 to 20 carbon atoms, an alkenyl radical having 2–20 carbon atoms, an aryl radical having 6 to 20 carbon atoms, an alkylaryl radical having 7 to 20 carbon atoms, an arylalkyl radical having 7 to 20 carbon atoms or an alkylsilyl radical having 3 to 20 carbon atoms.

In the general formula [1], as the grouping ($R_a$ Cp) and ($R'_b$ Cp) having the cyclopentadienyl skeleton, for example, cyclopentadienyl, methylcyclopentadienyl, ethylcyclopentadienyl, n-propylcyclopentadienyl, isopropylcyclopentadienyl, n-butylcyclopentadienyl, isobutylcyclopentadienyl, tert-butylcyclopentadienyl, 1,2-dimethylcyclopentadienyl, 1,3-dimethylcyclopentadienyl, 1,2,4-trimethylcyclopentadienyl, 1,2,3-trimethylcyclopentadienyl, tetramethylcyclopentadienyl, pentamethylcyclopentadienyl, trimethylsilylcyclopentadienyl, trimethylsilyltetramethylcyclopentadienyl, (phenyldimethylsilyl)cyclopentadienyl, triphenylsilylcyclopentadienyl, 1,3-di(trimethylsilyl) cyclopentadienyl, cyclohexylcyclopentadienyl, allylcyclopentadienyl, benzylcyclopentadienyl, phenylcyclopentadienyl, tolylcyclopentadienyl, indenyl, 1-methylindenyl, 2-methylindenyl, 2,4-dimethylindenyl, 4,7-dimethoxyindenyl, 4,7-dichloroindenyl, 5,6-dimethylindenyl, 2-methyl-4-ethyl-indenyl, 2-methyl-4,6-diisopropyl-indenyl, naphthylindenyl, 4,5,6,7-tetrahydroindenyl, 2-methyl-tetrahydroindenyl, fluorenyl, 2,7-di-tert-butylfluorenyl.

In the general formula [2], R" represents a divalent radical having 1 to 20 carbon atoms, which links ($R_d$ Cp) and ($R'_e$ Cp), and there are mentioned concretely alkylene, such as methylene, ethylene; alkylidene, such as ethylidene, propylidene, isopropylidene; arylalkylidene, such as phenylmethylidene, diphenylmethylidene; silylene, such as dimethylsilylene, diethylsilylene, dipropylsilylene, diisopropylsilylene, methylethylsilylene, methylisopropylsilylene, methyltert-butylsilylene, methylphenylsilylene, diphenylsilylene; germylene, such as dimethylgermylene, diethylgermylene, dipropylgermylene, diisopropylgermylene, diphenylgermylene, methylethylgermylene, methylisopropylgermylene, methyltert-butylgermylene, methylphenylgermylene, diphenylgermylene; alkylphophinediyl, such as methylphosphinediyl; alkylimino, such as methylimino; alkylboranediyl, such as methylborandiyl.

And, as the grouping R" ($R_d$ Cp) and ($R'_e$ Cp) having the cyclopentadienyl skeleton in the general formula [2], there are mentioned, for example, ethylenebisindenyl, diphenylmethylenebisindenyl, dimethylsilylenebisindenyl, isopropylidenebisindenyl, dimethylsilylenebistetrahydroindenyl, isopropylidenecyclopentadienyl-1-fluorenyl, diphenylmethylencyclopentadienyl-1-fluorenyl, dimethylsilylenecyclopentadienyl-1-fluorenyl, dimethylsilylenbis(2,3,5-trimethylcyclopentadienyl), dimethylsilylenebis(2,4-dimethylcyclopentadienyl), dimethylsilylenebis(3-methylcyclopentadienyl), isopropylidenecyclopentadienyl-methylcyclopentadienyl, isopropylidenecyclopentadienyl-2,3,5-trimethylcyclopentadienyl, diphenylmethylenecyclopentadienyl-methylcyclopentadienyl, diphenylmethylenecyclopentadienyl-2,4-dimethylcyclopentadienyl, diphenylmethylenecyclopentadienyl-2,3,5-trimethylcyclopentadienyl, dimethylsilylencyclopentadienyl-methylcyclopentadienyl, dimethylsilylenecyclopentadienyl-2,4-dimethylcyclopentadienyl, dimethylsilylenecyclopentadienyl-2,3,5-trimethylcyclopentadienyl, isopropylidene-2,4-dimethylcycropentadienyl-1-fluorenyl, diphenylmethylene- 2,4-dimethylcyclopentadienyl-1-fluorenyl, dimethylsilylene-2,4-dimethylcyclopentadienyl-1-fluorenyl, cyclohexylidenecyclopentadienyl-1-fluorenyl, dimethylgermylenebis-1-indenyl.

In the general formulae [1] and [2], Ph represents an aromatic radical, such as, for example, a benzene, naphthalene, anthrathene, indenyl, and phenanthrene ring.

Further, in the general formulae [1] and [2], the substituent Y is a radical which is selected from the group of a hydrogen atom, a hydrocarbon radical, a silyl radical, a halogen atom, a halogenated hydrocarbon radical, a nitrogen-containing organic radical, an oxygen-containing organic radical or a sulphur-containing organic radical. And more concretely, it is a hydrocarbon radical such as an alkyl having 1–10 carbon atoms, an aryl having 6–10 carbon atoms, an alkenyl having 2–10 carbon atoms, an alkynyl having 2–10 carbon atoms, an arylalkyl having 7–20 carbon atoms, an arylalkenyl having 8–20 carbon atoms and an alkylaryl having 7–20 carbon atoms, or a silyl radical such as an alkylsilyl, an arylsilyl and the like, wherein the alkyl radical may include various kind of geometric isomers including cycloalkyl, proviso that as mentioned above a hydrogen atom is excluded when Ph is a benzene ring.

When the substituent Y is a hydrocarbon atom, there are mentioned an alkyl radical having 1–10 carbon atoms such as, for example, methyl, ethyl, propyl, butyl, pentyl, hexyl, heptyl, octyl, nonyl, decyl, cyclohexyl, cyclooctyl, norbornyl; an aryl radical having 6–10 carbon atoms such as, for example, phenyl, naphthyl; an alkenylradical having 2–10 carbon atoms such as, for example, vinyl, propenyl; an alkynyl radical having 2–10 carbon atoms such as, for example, ethynyl, propynyl; an arylalkyl radical having 7–20 carbon atoms such as, for example, benzyl, phenethyl; an arylalkenyl radical having 8–20 carbon atoms such as, for example, stylyl, cinnamyl; and an alkylaryl radical having 7–20 carbon atoms such as, for example, tolyl, xylyl, mesyl, respectively.

When the substituent Y is an alkylsilyl radical, there are mentioned concretely, for example, trimethylsilyl and triethylsilyl radical, and when the substituent Y is an arylsilyl radical, there are mentioned a diphenylmethylsilyl and triphenylsilyl radical.

When the substutient Y is a halogen atom, there are mentioned concretely, for example, a fluorine, chlorine, bromine, iodine atom, and when the substutient Y is a halogenated hydrocarbon radical, there are mentioned concretely, for example, chloromethyl, fluoromethyl, bromomethyl, iodomethyl, dichloromethyl, difluoromethyl, dibromomethyl, diiodomethyl, trichloromethyl, trifluoromethyl, chlorodifluoromethyl, 2,2,2-trifluoroethyl, perfluoroethyl, perfluoropropyl, perfluorobutyl, chlorophenyl, fluorophenyl, bromophenyl, iodophenyl, perfluorophenyl, chlorotetrafluorophenyl radical.

When the substutient Y is a nitrogen-containing organic radical, there are mentioned concretely, for example, a cyano, nitro, nitroso, isocyanide, cyanate, isocyanate, N-methylamino, anilino, N,N-dimethylamino, N,N-diethylamino, N,N-dipropylamino, N,N-diphenylamino, formamide, acetamide, N-methylacetamide, N-phenylacetamide radical.

When the substutient Y is an oxygen-containing organic radical, there are mentioned concretely, for example, a methoxy, ethoxy, propoxy, butoxy, phenoxy, formyl, acetyl, propyonyl, butylyl, valeryl, pyvaloyl, acyloyl, benzoyl, methoxycarbonyl, ethoxycarbonyl, phenoxycarbonyl, acetoxy, benzoyloxy radical.

When the substutient Y is an sulphur-containing organic radical, there are mentioned concretely, for example, a methylthio, ethylthio, phenylthio, methylsulfinyl, ethylsulfinyl, benzenesulfiniyl, trisulfinyl, tolylsulfinyl, mesyl, tosyl radical.

The symbol of c in the general formulae [1] and [2] is a value which is selected from 1 to 5. In case c is 2 to 5 and the plural substutient Y are bonded together, the same and/or different substutient are available.

As the transition metal compounds according to the definition of the general formula [1] mentioned above, the following compounds may be exemplified: dicyclopentadienylbis(2-fluorophenoxy)zirconium, dicyclopentadienylbis(3-fluorophenoxy)zirconium, dicyclopentadienylbis(4-fluorophenoxy)zirconium, dicyclopentadienylbis(2-chlorophenoxy)zirconium, dicyclopentadienylbis(3-chlorophenoxy)zirconium, dicyclopentadienylbis(4-chlorophenoxy)zirconium, dicyclopentadienylbis(2-bromophenoxy)zirconium, dicyclopentadienylbis(3-bromophenoxy)zirconium, dicyclopentadienylbis(4-bromophenoxy)zirconium, dicyclopentadienylbis(2-iodophenoxy)zirconium, dicyclopentadienylbis(3-iodophenoxy)zirconium, dicyclopentadienylbis(4-iodophenoxy)zirconium, dicyclopentadienylbis(2,3-difluorophenoxy)zirconium, dicyclopentadienylbis(2,4-difluorophenoxy)zirconium, dicyclopentadienylbis(2 5-difluorophenoxy)zirconium, dicyclopentadienylbis(2,6-difluorophenoxy)zirconium, dicyclopentadienylbis(3,4-difluorophenoxy)zirconium, dicyclopentadienylbis(3,5-difluorophenoxy)zirconium, dicyclopentadienylbis(2,3-dichlorophenoxy)zirconium, dicyclopentadienylbis(2,4-dichlorophenoxy)zirconium, dicyclopentadienylbis(2,5-dichlorophenoxy)zirconium, dicyclopentadienylbis(2,6-dichlorophenoxy)zirconium, dicyclopentadienylbis(3,4-dichlorophenoxy)zirconium, dicyclopentadienylbis(3,5-dichlorophenoxy)zirconium, dicyclopentadienylbis(2,3,4-trifluorophenoxy)zirconium, dicyclopentadienylbis(2,3,5-trifluorophenoxy)zirconium, dicyclopentadienylbis(2,3,6-trifluorophenoxy)zirconium, dicyclopentadienylbis(2,4,5-trifluorophenoxy)zirconium, dicyclopentadienylbis(2,4,6-trifluorophenoxy)zirconium, dicyclopentadienylbis(3,4,5-trifluorophenoxy)zirconium, dicyclopentadienylbis(2,3,5,6-tetrafluorophenoxy)zirconium, dicyclopentadienylbis(pentafluorophenoxy)zirconium, dicyclopentadienylbis(2-fluoromethylphenoxy)zirconium, dicyclopentadienylbis(3-fluoromethylphenoxy)zirconium, dicyclopentadienylbis(4-fluoromethylphenoxy)zirconium, dicyclopentadienylbis(2-chloromethylphenoxy)zirconium, dicyclopentadienylbis(3-chloromethylphenoxy)zirconium, dicyclopentadienylbis(4-chloromethylphenoxy)zirconium, dicyclopentadienylbis(2-trifluoromethylphenoxy)zirconium, dicyclopentadienylbis(3-trifluoromethylphenoxy)zirconium, dicyclopentadienylbis,(4-trifluoromethylhenoxy)zirconium, dicyclopentadienylbis(3,5-di-trifluoromethyl)phenoxy)zirconium, dicyclopentadienylbis(2-(2,2,2-trifluoroethyl)phenoxy)zirconium, dicyclopentadienylbis(3-(2,2,2-trifluoroethyl)phenoxy)zirconium, dicyclopentadienylbis(4-(2,2,2-trifluoroethyl)phenoxy)zirconium, dicyclopentadienylbis(2-trichloromethylphenoxy)zirconium, dicyclopentadienylbis(3-trichloromethylphenoxy)zirconium, dicyclopentadienylbis(4-methylphenoxy)zirconium dicyclopentadienylbis(2-methylphenoxy)zirconium, dicyclopentadienylbis(3-methylphenoxy)zirconium, dicyclopentadienylbis(4-methylphenoxy)zirconium, dicyclopentadienylbis(2,3dimethylphenoxy)zirconium, dicyclopentadienylbis(2,4-dimethylphenoxy)zirconium, dicyclopentadienylbis(2,5-dimethylphenoxy)zirconium, dicyclopentadienylbis(2,4- dimethylphenoxy)zirconium, dicyclopentadienylbis(3,4-dimethylphenoxy)zirconium, dicyclopentadienylbis(3,5-dimethylphenoxy)zirconium, dicyclopentadienylbis(2,3,4-trimethylphenoxy)zirconium, dicyclopentadienylbis(2,3,5-trimethylphenoxy)zirconium, dicyclopentadienylbis(2,3,6-trimethylphenoxy)zirconium, dicyclopentadienylbis(2,4,5-trimethylphenoxy)zirconium, dicyclopentadienylbis(2,4,6-trimethylphenoxy)zirconium, dicyclopentadienylbis(3,4,5-trimethylphenoxy)zirconium, dicyclopentadienylbis(pentamethylphenoxy)zirconium, dicyclopentadienylbis(2-methyl-4-fluorophenoxy)zirconium, dicyclopentadienylbis(2-chloro-4-fluorophenoxy)zirconium, dicyclopentadienylbis(2-chloro-4-trifluoromethylphenoxy)zirconium, dicyclopentadienylbis(2-fluoro-4-trifluoromethylphenoxy)zirconium, dicyclopentadienylbis(2-trifluoromethyl-4-florophenoxy)zirconium, dicyclopentadienylbis(2-ethylphenoxy)zirconium, dicyclopentadienylbis(3-ethylphenoxy)zirconium, dicyclopentadienylbis(4-ethylphenoxy)zirconium, dicyclopentadienylbis(2-isopropylphenoxy)zirconium, dicyclopentadienylbis(3-isopropylphenoxy)zirconium, dicyclopentadienylbis(4-isopropylphenoxy)zirconium, dicyclopentadienylbis(2-tert-butylphenoxy)zirconium, dicyclopentadienylbis(3-tert-butylphenoxy)zirconium, dicyclopentadienylbis(4-tert-butylphenoxy)zirconium, dicyclopentadienylbis(3,5-di-tert-butylphenoxy)zirconium, dicyclopentadienylbis(2-trimethylsilylphenoxy)zirconium, dicyclopentadienylbis(3-trimethylsilylphenoxy)zirconium, dicyclopentadienylbis(4-trimethylsilylphenoxy)zirconium, dicyclopentadienylbis(2-cyclohexylphenoxy)zirconium, dicyclopentadienylbis(3-cyclohexylphenoxy)zirconium, dicyclopentadienylbis(4-cyclohexylphenoxy)zirconium, dicyclopentadienylbis(1-naphthyloxy)zirconium, dicyclopentadienylbis(2-naphthyloxy)zirconium, dicyclopentadienylbis(8-trifluorometh-1-naphthyloxy)zirconium, dicyclopentadienylbis(2,8-dimethyl-1-naphthyloxy)zirconium, dicyclopentadienylbis(1-tert-butyl-2-naphthyloxy)zirconium, dicyclopentadienylbis(8-bromo-2-naphthyloxy)zirconium, dicyclopentadienylbis(2-phenylphenoxy)zirconium, dicyclopentadienylbis(3-phenylphenoxy)zirconium, dicyclopentadienylbis(4-phenylphenoxy)zirconium, dicyclopentadienylbis(2-benzylphenoxy)zirconium, dicyclopentadienylbis(3-benzylphenoxy)zirconium, dicyclopentadienylbis(4-benzylphenoxy)zirconium, dicyclopentadienylbis(2-tolylphenoxy)zirconium, dicyclopentadienylbis(3-tolylphenoxy)zirconium, dicyclopentadienylbis(4-tolylphenoxy)zirconium, dicyclopentadienylbis(2-vinylphenoxy)zirconium, dicyclopentadienylbis(3-vinylphenoxy)zirconium, dicyclopentadienylbis(4-vinylphenoxy)zirconium, dicyclopentadienylbis(2-(2-propenyl)phenoxy)zirconium, dicyclopentadienylbis(3-(2-propenyl)phenoxy)zirconium, dicyclopentadienylbis(4-(2-propenyl)phenoxy)zirconium, dicyclopentadienylbis(2-methyl-6-(2-propenyl)phenoxy)zirconium, dicyclopentadienylbis(2-ethynylphenoxy)zirconium, dicyclopentadienylbis(3-ethynylphenoxy)zirconium, dicyclopentadienylbis(4-ethynylphenoxy)zirconium, dicyclopentadienylbis(2-methoxyphenoxy)zirconium, dicyclopentadienylbis(3-methoxyphenoxy)zirconium, dicyclopentadienylbis(4-methoxyphenoxy)zirconium, dicyclopentadienylbis(2-tert-butoxyphenoxy)zirconium, dicyclopentadienylbis(3-tert-butoxyphenoxy)zirconium, dicyclopentadienylbis(4-tert-butoxyphenoxy)zirconium, dicyclopentadienylbis(2-phenoxyphenoxy)zirconium, dicyclopentadienylbis(3-phenoxyphenoxy)zirconium, dicyclopentadienylbis(4-phenoxyphenoxy)zirconium, dicyclopentadienylbis(2-formylphenoxy)zirconium, dicyclopentadienylbis(3-formylphenoxy)zirconium, dicyclopentadienylbis(4-formylpwhenoxy)zirconium, dicyclopentadienylbis(2-acetylphenoxy)zirconium, dicyclopentadienylbis(3-acetylphenoxy)zirconium, dicyclopentadienylbis(4-acetylphenoxy)zirconium, dicyclopentadienylbis(2-benzoylphenoxy)zirconium, dicyclopentadienylbis(3-benzoylphenoxy)zirconium, dicyclopentadienylbis(4-benzoylphenoxy)zirconium, dicyclopentadienylbis(2-methoxycarbonylphenoxy)zirconium, dicyclopentadienylbis(3-methoxycarbonylphenoxy)zirconium, dicyclopentadienylbis(4-methoxycarbonylphenoxy)zirconium, dicyclopentadienylbis(2-aetoxyphenoxy)zirconium, dicyclopentadienylbis(3-acetoxyphenoxy)zirconum, dicyclopentadienylbis(4-acetoxyphenoxy)zirconium, dicyclopentadienylbis(2-cyanophenoxy)zirconium, dicyclopentadienylbis(3-cyanophenoxy)zirconium, dicyclopentadienylbis(4-cyanophenoxy)zirconium, dicyclopentadienylbis(2-nitrophenoxy)zirconium, dicyclopentadienylbis(3-nitrophenoxy)zirconium, dicyclopentadienylbis(4-nitrophenoxy)zirconium, dicyclopentadienylbis(2-anilinophenoxy)zirconium, dicyclopentadienylbis(3-anilinophenoxy)zirconium, dicyclopentadienylbis(4-anilinophenoxy)zirconium, dicyclopentadienylbis(2-dimethylaminophenoxy)zirconium, dicyclopentadienylbis(3-dimethylaminophenoxy)zirconium, dicyclopentadienylbis(4-dimethylaminophenoxy)zirconium, dicyclopentadienylbis(2-dimethylaminomethylphenoxy)zirconium, dicyclopentadienylbis(3-dimethylaminomethylphenoxy)zirconium, dicyclopentadienylbis(4-dimethylaminomethylphenoxy)zirconium, dicyclopentadienylbis(2-formylaminophenoxy)zirconium, dicyclopentadienylbis(3-formylaminophenoxy)zirconium, dicyclopentadienylbis(4-formylaminophenoxy)zirconium, dicyclopentadienylbis(2-acetylaminophenoxy)zirconium, dicyclopentadienylbis(3-acetylaminophenoxy)zirconium, dicyclopentadienylbis(4-acetylaminophenoxy)zirconium, dicyclopentadienylbis(2-thiomethoxyphenoxy)zirconium, dicyclopentadienylbis(3-thiomethoxyphenoxy)zirconium, dicyclopentadienylbis(4-thiomethoxyphenoxy)zirconium, dicyclopentadienylbis(2-thiophenoxyphenoxy)zirconium, dicyclopentadienylbis(3-thiophenoxyphenoxy)zirconium, dicyclopentadienylbis(4-thiophenoxyphenoxy)zirconium, dicyclopentadienylbis(2-methylsulfinylphenoxy)zirconium, dicyclopentadienylbis(3-methylsulfinylphenoxy)zirconium, dicyclopentadienylbis(4-methylsulfinylphenoxy)zirconium, dicyclopentadienylbis(2-mesylphenoxy)zirconium, dicyclopentadienylbis(3-mesylphenoxy)zirconium, dicyclopentadienylbis(4-mesylphenoxy)zirconium, dicyclopentadienylbis(2-tosylphenoxy)zirconium, dicyclopentadienylbis(3-tosylphenoxy)zirconium, dicyclopentadienylbis(4-tosylphenoxy)zirconium, dicyclopentadienylbis(2-trifluoromethanesulfonylphenoxy)zirconium, dicyclopentadienylbis(3-trifluoromethanesulfonylphenoxy)zirconium, dicyclopentadienylbis(4-trifluoromethanesulfonylphenoxy)zirconium, dicyclopentadienylbis(2-methylthiophenoxy)zirconium, dicyclopentadienylbis(3-methylthiophenoxy)zirconium, dicyclopentadienylbis(4-methylthiophenoxy)zirconium, dicyclopentadienylbis(2-tert-butylthiophenoxy)zirconium, dicyclopentadienylbis(3-tert-butylthiophenoxy)zirconium, dicyclopentadienylbis(4-tert-butylthiophenoxy)zirconium, dicyclopentadienylbis(2-fluorothiophenoxy)zirconium, dicyclopentadienylbis(3-fluorothiophenoxy)

zirconium, dicyclopentadienylbis(4-fluorothiophenoxy)zirconium, dicyclopentadienylbis(2-chlorothiophenoxy)zirconium, dicyclopentadienylbis(3-chlorothiophenoxy)zirconium, dicyclopentadienylbis(4-chlorothiophenoxy)zirconium, dicyclopentadienylbis(2-trifluoromethylthiophenoxy)zirconium, dicyclopentadienylbis(3-trifluoromethylthiophenoxy)zirconium, dicyclopentadienylbis(4-trifluoromethylthiophenoxy)zirconium, dicyclopentadienylbis(2-methoxythiophenoxy)zirconium, dicyclopentadienylbis(3-methoxythiophenoxy)zirconium, dicyclopentadienylbis(4-methoxythiophenoxy)zirconium, bis(methylcyclopentadienyl)bis(2-chlorophenoxy)zirconium, bis(methylcyclopentadienyl)bis(3-chlorophenoxy)zirconium, bis(methylcyclopentadienyl)bis(4-chlorophenoxy)zirconium, bis(methylcyclopentadienyl)bis(2-trifluoromethylphenoxy)zirconium, bis(methylcyclopentadienyl)bis(3-trifluoromethylphenoxy)zirconium, bis(methylcyclopentadienyl)bis(4-trifluoromethylphenoxy)zirconium, bis(methylcyclopentadienyl)bis(2-phenylphenoxy)zirconium, bis(methylcyclopentadienyl)bis(3-phenylphenoxy)zirconium, bis(methylcyclopentadienyl)bis(4-phenylphenoxy)zirconium, bis(1,2-dimethylcyclopentadienyl)bis(2-ethylphenoxy)zirconium, bis(1,2-dimethylcyclopentadienyl)bis(3-ethylphenoxy)zirconium, bis(1,2-dimethylcyclopentadienyl)bis(4-ethylphenoxy)zirconium, bis(1,2-dimethylcyclopentadienyl)bis(2,4-diethylphenoxy)zirconium, bis(1,2-dimethylcyclopentadienyl)bis(2,5-diethylphenoxy)zirconium, bis(1,2-dimethylcyclopentadienyl)bis(2-cyanophenoxy)zirconium, bis(1,2-dimethylcyclopentadienyl)bis(3-cyanophenoxy)zirconium, bis(1,2-dimethylcyclopentadienyl)bis(4-cyanophenoxy)zirconium, bis(1,2-dimethylcyclopentadienyl)bis(2-bromophenoxy)zirconium, bis(1,2-dimethylcyclopentadienyl)bis(3-bromophenoxy)zirconium, bis(1,2-dimethylcyclopentadienyl)bis(4-bromophenoxy)zirconium, bis(1,3-dimethylcyclopentadienyl)bis(2-trifluoromethylphenoxy)zirconium, bis(1,3-dimethylcyclopentadienyl)bis(3-trifluoromethylphenoxy)zirconium, bis(1,3-dimethylcyclopentadienyl)bis(4-trifluoromethylphenoxy)zirconium, bis(1,3-dimethylcyclopentadienyl)bis(2-tert-butylphenoxy)zirconium, bis(1,3-dimethylcyclopentadienyl)bis(3-tert-butylphenoxy)zirconium, bis(1,3-dimethylcyclopentadienyl)bis(4-tert-butylphenoxy)zirconium, bis(1,3-dimethylcyclopentadienyl)bis(2-chlorophenoxy)zirconium, bis(1,3-dimethylcyclopentadienyl)bis(3-chlorophenoxy)zirconium, bis(1,3-dimethylcyclopentadienyl)bis(4-chlorophenoxy)zirconium, bis(1,2,3-trimethylcyclopentadienyl)bis(2-fluorophenoxy)zirconium, bis(1,2,3-trimethylcyclopentadienyl)bis(3-fluorophenoxy)zirconium, bis(1,2,3-trimethylcyclopentadienyl)bis(4-fluorophenoxy)zirconium, bis(1,2,3-trimethylcyclopentadienyl)bis(2-isopropylphenoxy)zirconium, bis(1,2,3-trimethylcyclopentadienyl)bis(3-isopropylphenoxy)zirconium, bis(1,2,3-trimethylcyclopentadienyl)bis(4-isopropylphenoxy)zirconium, bis(1,2,3-trimethylcyclopentadienyl)bis(2-nitrophenoxy)zirconium, bis(1,2,3-trimethylcyclopentadienyl)bis(3-nitrophenoxy)zirconium, bis(1,2,3-trimethylcyclopentadienyl)bis(4-nitrophenoxy)zirconium, bis(1,2,4-trimethylcyclopentadienyl)bis(2-trifluoromethylphenoxy)zirconium, bis(1,2,4-trimethylcyclopentadienyl)bis(3-trifluoromethylphenoxy)zirconium, bis(1,2,4-trimethylcyclopentadienyl)bis(4-trifluoromethylphenoxy)zirconium, bis(1,2,4-trimethylcyclopentadienyl)bis(2-methylphenoxy)zirconium, bis(1,2,4-trimethylcyclopentadienyl)bis(3-methylphenoxy)zirconium, bis(1,2,4-trimethylcyclopentadienyl)bis(4-methylphenoxy)zirconium, bis(1,2,4-trimethylcyclopentadienyl)bis(2,4-dimethylphenoxy)zirconium, bis(1,2,4-trimethylcyclopentadienyl)bis(2,4-dichlorophenoxy)zeirconium, bis(1,2,4-trimethylcyclopentadienyl)bis(2-tert-butylphenoxy)zirconium, bis(1,2,4-trimethylcyclopentadienyl)bis(3-tert-butylphenoxy)zirconium, bis(1,2,4-trimethylcyclopentadienyl)bis(4-tert-butylphenoxy)zirconium, bis(1,2,3,4-tetramethylcyclopentadienyl)bis(2-methoxyphenoxy)zirconium, bis(1,2,3,4-tetramethylcyclopentadienyl)bis(3-methoxyphenoxy)zirconium, bis(1,2,3,4-tetramethylcyclopentadienyl)bis(4-methoxyphenoxy)zirconium, bis(1,2,3,4-tetramethylcyclopentadienyl)bis(2-iodophenoxy)zirconium, bis(1,2,3,4-tetramethylcyclopentadienyl)bis(3-iodophenoxy)zirconium, bis(1,2,3,4-tetramethylcyclopentadienyl)bis(4-iodophenoxy)zirconium, bis(1,2,3,4-tetramethylcyclopentadienyl)bis(2-thiomethylphenoxy)zirconium, bis(1,2,3,4-tetramethylcyclopentadienyl)bis(3-thiomethylphenoxy)zirconium, bis(1,2,3,4-tetramethylcyclopentadienyl)bis(4-thiomethylphenoxy)zirconium, bis(pentamethylcyclopentadienyl)bis(2-fluorophenoxy)zirconium, bis(pentamethylcyclopentadienyl)bis(3-fluorophenoxy)zirconium, bis(pentamethhylcycllpentadienyl)bis(4-fluorophenoxy)zirconium, bis(ethylcyclopentadienyl)bis(2-ethylphenoxy)zirconium, bis(ethylcyclopentadienyl)bis(3-ethylphenoxy)zirconium, bis(ethylcyclopentadienyl)bis(4-ethylphenoxy)zirconium, bis(isopropylcyclopentadienyl)bis(2-acetylphenoxy)zirconium, bis(isopropylcyclopentadienyl)bis(3-acetylphenoxy)zirconium, bis(isopropylcyclopentadienyl)bis(4-acetylphenoxy)zirconium, bis(isopropylcyclopentadienyl)bis(2-methylphenoxy)zirconium, bis(isopropylcyclopentadienyl)bis(3-methylphenoxy)zirconium, bis(isopropylcyclopentadienyl)bis(4-methylphenoxy)zirconium, bis(n-butylcyclopentadienyl)bis(2-chlorophenoxy)zirconium, bis(n-butylcyclopentadienyl)bis(3-chlorophenoxy)zirconium, bis(n-butylcyclopentadienyl)bis(4-chlorophenoxy)zirconium, bis(n-butylcyclopentadienyl)bis(2-trifluoromethylphenoxy)zirconium, bis(n-butylcyclopentadienyl)bis(3-trifluoromethylphenoxy)zirconium, bis(n-butylcyclopentadienyl)bis(4-trifluoromethylphenoxy)zirconium, bis(n-butylcyclopentadienyl)bis(2-tert-butylphenoxy)zirconium, bis(n-butylcyclopentadienyl)bis(3-tert-butylphenoxy)zirconium, bis(n-butylcyclopentadienyl)bis(4-tert-butylphenoxy)zirconium, bis(n-butylcyclopentadienyl)bis(2-cyanophenoxy)zirconium, bis(n-butylcyclopentadienyl)bis(3-cyanophenoxy)zirconium, bis(n-butylcyclopentadienyl)bis(4-cyanophenoxy)zirconium, bis(tert-butylcyclopentadienyl)bis(2-fluorophenoxy)zirconium, bis(tert-butylcyclopentadienyl)bis(3-fluorophenoxy)zirconium, bis(tert-butylcyclopentadienyl)bis(4-fluorophenoxy)zirconium, bis(tert-butylcyclopentadienyl)bis(2-ethylphenoxy)zirconium, bis(tert-butylcyclopentadienyl)bis(3-ethylphenoxy)zirconium, bis(tert-butylcyclopentadienyl)bis(4-ethylphenoxy)zirconium, bis(tert-butylcyclopentadienyl)bis(2,4-dimethylphenoxy)zirconium, bis(1,3-di-tert-butylcyclopentadienyl)bis(2- chlorophenoxy)zirconium, bis(1,3-di-tert-butylcyclopentadienyl)bis(3-chlorophenoxy)zirconium, bis(1,3-di-tert-butylcyclopentadienyl)bis(4-chlorophenoxy)zirconium, bis(1,3-di-tert-butylcyclopentadienyl)bis(2-trifluoromethylphenoxy)zirconium, bis(1,3-di-tert-butylcyclopentadienyl)bis(3-trifluoromethylphenoxy)zirconium, bis(1,3-di-tert-butylcyclopentadienyl)bis(4-trifluoromethylphenoxy)zirconium, bis(phenylcyclopentadienyl)bis(2-phenylphenoxy)zirconium, bis(phenylcyclhpentadienyl)bis(3-phenylphenoxy)zirconium, bis(phenylcyclopentadienyl)bis(4-phenylphenoxy)zirconium, bis(phenylcyclopentadienyl)bis(2,4-dichlorophenoxy)zirconium, bis(trimethylsilylcyclopentadienyl)bis(2-tert-butoxyphenoxy)zirconium, bis(trimethylsilylcyclopentadienyl)bis(3-tert-butoxyphenoxy)zirconium, bis(trimethylsilylcyclopentadienyl)bis(4-tert-butoxyphenoxy)zirconium, bis(trimethylsilylcyclopentadienyl)bis(2-phenylphenoxy)zirconium, bis(trimethylsilylcyclopentadienyl)bis(3-phenylphenoxy)zirconium, bis(trimethylsilylcyclopentadienyl)bis(4-phenylphenoxy)zirconium, bis(trimethylsilylcyclopentadienyl)bis(2,4-di-fluorophenoxy)zirconium, bis(cyclohexylcyclopentadienyl)bis(2-iodophenoxy)zirconium, bis(cyclohexylcyclopentadienyl)bis(3-iodophenoxy)zirconium, bis(cyclohexylcyclopentadienyl)bis(4-iodophenoxy)zirconium, bis(indenyl)bis(2-methylphenoxy)zirconium, bis(indenyl)bis(3-methylphenoxy)zirconium, bis(indenyl)bis(4-methylphenoxy)zirconium, bis(1-methylindenyl)bis(2-fluorophenoxy)zirconium, bis(1-methylindenyl)bis(3-fluorophenoxy)zirconium, bis(1-methylindenyl)bis(4-fluorophenoxy)zirconium, bis(2-methylindenyl)bis(2-bromophenoxy)zirconium, bis(2-methylindenyl)bis(3-bromophenoxy)zirconium, bis(2-methylindenyl)bis(4-bromophenoxy)zirconium, bis(5,6-dimethylindenyl)bis(2-isopropylphenoxy)zirconium, bis(5,6-dimethylindenyl)bis(3-isopropylphenoxy)zirconium, bis(5,6-dimethylindenyl)bis(4-isopropylphenoxy)zirconium, bis(5,6-dimethoxyindenyl)bis(2-cyanophenoxy)zirconium, bis(5,6-dimethoxyindenyl)bis(3-cyanophenoxy)zirconium, bis(5,6-dimethoxyindenyl)bis(4-cyanophenoxy)zirconium, bis(fluorenyl)bis(2-chlorophenoxy)zirconium, bis(fluorenyl)bis(3-chlorophenoxy)zirconium, bis(fluorenyl)bis(4-chlorophenoxy)zirconium, bis(4,5,6,7-tetrahydroindenyl)bis(2-tert-butylphenoxy)zirconium, bis(4,5,6,7-tetrahydroindenyl)bis(3-tert-butylphenoxy)zirconium, bis(4,5,6,7-tetrahydroindenyl)bis(4-tert-butylphenoxy)zirconium, bis(2-methyltetrahydroindenyl)bis(2-nitrophenoxy)zirconium, bis(2-methyltetrahydroindenyl)bis(3-nitrophenoxy)zirconium, bis(2-methyltetrahydroindenyl)bis(4-nitrophenoxy)zirconium, bis(2,7-di-tert-butylfluorenyl)bis(2-trifluoromethylphenoxy)zirconium, bis(2,7-di-tert-butylfluorenyl)bis(3-trifluoromethylphenoxy)zirconium, bis(2,7-di-tert-butylfluorenyl)bis(4-trifluoromethylphenoxy)zirconium, etc.

Further, in the present invention, the transition metal compounds may be used similarly, in which the zirconium atom in the zirconium compound of the general formula [1] as exemplified is substituted by a titanium or hafnium atom.

On the other hand, as the transition metal compounds represented by the general formula [2], the following compounds may be exemplified: ethylenebis(indenyl)bis(4-trifluoromethylphenoxy)zirconium, ethylenebis(indenyl)bis(4-fluorophenoxy)zirconium, ethylenebis(indenyl)bis(4-chlorophenoxy)zirconium, ethylenebis(indenyl)bis(2-fluorophenoxy)zirconium, ethylenebis(3-methylindenyl)bis(4-trifluoromethylphenoxy)zirconium, ethylenebis(3-methylindenyl)bis(4-fluorophenoxy)zirconium, ethylenebis(3-methylindenyl)bis(4-chlorophenoxy)zirconium, ethylenebis(3-methylindenyl)bis(2-fluorophenoxy)zirconium, ethylenebis(5,6-dimethylindenyl)bis(4-trifluoromethylphenoxy)zirconium, ethylenebis(5,6-dimethylindenyl)bis(4-fluorophenoxy)zirconium, ethylenebis(5,6-dimethylindenyl)bis(4-chlorophenoxy)zirconium, ethylenebis(5,6-dimethylindenyl)bis(2-fluorophenoxy)zirconium, ethylenebis(4,7-dimethylindenyl)bis(4-trifluoromethylphenoxy)zirconium, ethylenebis(4,7-dimethylindenyl)bis(4-fluorophenoxy)zirconium, ethylenebis(5,6-dimethoxylindenyl)bis(4-trifluoromethylphenoxy)zirconium, ethylenebis(5,6-dimethoxylindenyl)bis(4-fluorophenoxy)zirconium, ethylenebis(5,6-dihydroindenyl)bis(4-trifluoromethylphenoxy)zirconium, ethylenebis(5,6-dihydroindenyl)bis(4-fluorophenoxy)zirconium, ethylenebis(5,6-dihydroindenyl)bis(4-chlorophenoxy)zirconium, ethylenebis(5,6-dihydroindenyl)bis(2-fluorophenoxy)zirconium, ethylenebis(4,5,6,7-tetrahydroindenyl)bis(4-trifluoromethylphenoxy)zirconium, ethylenebis(4,5,6,7-tetrahydroindenyl)bis(4-fluorophenoxy)zirconium, ethylenebis(4,5,6,7-tetrahydroindenyl)bis(4-chlorophenoxy)zirconium, ethylenebis(4,5,6,7-tetrahydroindenyl)bis(2-fluorophenoxy)zirconium, methylenebis(cyclopentadienyl)bis(2-fluorophenoxy)zirconium, methylenebis(cyclopentadienyl)bis(2-ethylphenoxy)zirconium, methylenebis(methylcyclopentadienyl)bis(3-chlorophenoxy)zirconium, methylenbis(1,3-dimethylcyclopentadienyl)bis(2-trifluoromethylphenoxy)zirconium, methylenbis(n-butylcyclopentadienyl)bis(4-tert-butylphenoxy)zirconium, ethylenbis(3-methylcyclopentadienyl)bis(4-trifluoromethylphenoxy)zirconium, ethylenbis(3-methylcyclopentadienyl)bis(4-fluorophenoxy)zirconium, ethylenbis(3-isopropylcyclopentadienyl)bis(4-trifluoromethylphenoxy)zirconium, ethylenbis(3-isopropylcyclopentadienyl)bis(4-fluorophenoxy)zirconium, ethylenbis(3-tert-butylcyclopentadienyl)bis(4-trifluoromethylphenoxy)zirconium, ethylenbis(3-tert-butylcyclopentadienyl)bis(4-fluorophenoxy)zirconium, isopropylidene(cyclopentadienyl)(indenyl)bis(4-trifluoromethylphenoxy)zirconium, isopropylidene(cyclopentadienyl)(indenyl)bis(4-fluorophenoxy)zirconium, isopropylidene(methylcyclopentadienyl)(indenyl)bis(4-trifluoromethylphenoxy)zirconium, isopropylidene(methylcyclopentadienyl)(indenyl)bis(4-fluorophenbxy)zirconium, isopropylidenebis(indenyl)bis(4-trifluoromethylphenoxy)zirconium, isopropylidenebis(indenyl)bis(4-fluorophenoxy)zirconium, isopropylidene(cyclopentadienyl)(fluorenyl)bis(4-trifluoromethylphenoxy)zirconium, isopropylidene(cyclopentadienyl)(fluorenyl)bis(4-fluorophenoxy)zirconium, isopropylidene(3-methylcyclopentadienyl)(fluorenyl)bis(4-trifluoromethylphenoxy)zirconium, isopropylidene(3-methylcyclopentadienyl)(fluorenyl)bis(4-fluorophenoxy)zirconium, tetramethylethylidenebis(2-tert-butylcyclopentadienyl)bis(4-trifluoromethylphenoxy)zirconium, tetramethylethylidenebis(2-tert-butylcyclopentadienyl)bis(4-fluorophenoxy)zirconium, dimethylsilylenebis(indenyl)bis(4-trifluoromethylphenoxy)zirconium, dimethylsilylenebis(indenyl)bis(4-fluorophenoxy)zirconium, dimethylsilylenebis(2-methylidenyl)bis(4-trifluoromethylphenoxy)zirconium, dimethylsilylenebis(2-methylindenyl)bis(4-fluorophenoxy)zirconium, dimethylsilylenebis(2-ethlyenylidenyl)bis(4- trifluoromethylphenoxy)zirconium, dimethylsilylenebis(2-ethylindenyl)bis(4-fluorophenoxy)zirconium, dimethylsilylenebis(2-methyl-5-isopropylindenyl)bis(4-trifluoromethylphenoxy)zirconium, dimethylsilylenebis(2-methyl-5-isopropylindenyl)bis(4-fluorophenoxy)zirconium, dimethylsilylenebis(4,5,6,7-tetrahydroindenyl)bis(4-trifluoromethylphenoxy)zirconium, dimethylsilylenebis(4,5,6,7-tetrahydroindenyl)bis(4-fluorophenoxy)zirconium, dimethylsilylenebis(2-tert-butylcyclopentadienyl)bis(4-trifluoromethylphenoxy)zirconium, dimethylsilylenebis(2-tert-butylcyclopentadienyl)bis(4-fluorophenoxy)zirconium, dimethylsilylenebis(2-tert-butyl-4-methylcyclopentadienyl)bis(4-fluorophenoxy)zirconium, dimethylsilylenebis(2-isopropyl-4-methylcyclopentadienyl)bis(4-fluorophenoxy)zirconium, dimethylsilylene(2,3,5-trimethylcyclopentadienyl)(2,4,5-trimethylcyclopentadienyl)bis(4-fluorophenoxy)zirconium, dimethylsilylene(2,4-dimethylcyclopentadienyl)(3,5-dimethylcyclopentadienyl)bis(4-fluorophenoxy)zirconium, dimethylsilylene(3-tert-butylcyclopentadienyl)(4-tert-butylcyclopentadienyl)bis(4-fluorophenoxy)zirconium, dimethylsilylene(3-methylcyclopentadienyl)(4-methylcyclopentadienyl)bis(4-fluorophenoxy)zirconium, dimethylsilylene(2,4-dimethylcyclopentadienyl)(3-methylcyclopentadienyl)bis(4-fluorophenoxy)zirconium, dimethylsilylene(2,4-dimethylcyclopentadienyl)(4-methylcyclopentadienyl)bis(4-fluorophenoxy)zirconium, dimethylsilylene(3,4-dimethylcyclopentadienyl)(3-methylcyclopentadienyl)bis(4-fluorophenoxy)zirconium, dimethylsilylene(3-tert-butylcyclopentadienyl)(3-methylcyclopentadienyl)bis(4-fluorophenoxy)zirconium, dimethylsilylene(3-tert-butylcyclopentadienyl)(4-methylcyclopentadienyl)bis(4-fluorophenoxy)zirconium, dimethylsilylene(2,3,5-trimethylcyclopentadienyl)(cyclopentadienyl)bis(4-fluorophenoxy)-zirconium, dimethylsilylene(2,4-dimethylcyclopentadienyl)(cyclopentadienyl)bis(4-fluorophenoxy)zirconium, dimethylsilylene(3-tert-butylcyclopentadienyl)(cyclopentadienyl)bis(4-fluorophenoxy)zirconium, dimethylsilylene(3-methylcyclopentadienyl)(cyclopentadienyl)bis(4-fluorophenoxy)zirconium, dimethylsilylene(cyclopentadienyl)(indenyl)bis(4-trifluoromethylphenoxy)zirconium, dimethylsilylene(cyclopentadienyl)(indenyl)bis(4-fluorophenoxy)zirconium, diphenylsilylenebis(indenyl)bis(4-trifluoromethylphenoxy)zirconium, diphenylsilylenebis(indenyl)bis(4-fluorophenoxy)zirconium, dibenzylsilylenebis(indennyl)bis(4-trifluoromethylphenoxy)zirconium, dibenzylsilylenebis(indenyl)bis(4-fluorophenoxy)zirconium, methylphenylsilylenebis(2-methylindenyl)bis(4-trifluoromethylphenoxy)zirconium, methylphenylsilylenebis(2-methylindenyl)bis(4-fluorophenoxy)zirconiumu, dimethylsilylenebis(3,4-dimethylcyclopentadienyl)bis(4-trifluoromethylphenoxy)zirconium, dimethylsilylenebis(3,4-dimethylcyclopentadienyl)bis(4-fluorophenoxy)zirconium, dimethylsilylenebis(4,5,6,7-tetrahydroindenyl)bis(4-trifluoromethylphenoxy)zirconium, dimethylsilylenebis(4,5,6,7-tetrahydroindenyl)bis(4-fluorophenoxy)zirconium.

The transition metal compounds, in which the zirconium atom of the zirconium compounds as mentioned above of the formula [2] is substituted by a titanium or hafnium atom, also may be used similarly.

The transition metal compounds according to the present invention may be synthesized by some known processes. The transition metal compound represented by the general formula [1] is synthesized, for example, by a process in which the IVA group transition metal compound represented by the general formula [3] is reacted at first with alkyl lithium to form the reactive intermediate compound of the general formula [4]. Then, the intermediate compound is reacted with an aromatic hydroxy or thiol compound having a specified substituent represented by the general formula [5] to form a final transition metal compound according to the reaction equation [6]:

$(R_a\ Cp)_m(R'_b\ Cp)_nMZ_{4-(m+n)}$ [3]

wherein $R_a$ Cp and $R'_b$ Cp each represents a grouping having the cyclopentadienyl skeleton, M is titanium, zirconium or hafnium, Z is a halogen atom, each of a and b is an integer of 0–5, each of m and n is an integer of 0–3, and m+n is an integer of 1–3;

$(R_a\ CP)_m(R'_b\ Cp)_n\ MQ_{4-(m+n)}$ [4]

wherein $(R_a\ Cp)$ and $(R'_b\ Cp)$, M, a, b, m and n each has the same meaning as in the general formula [3] and Q represents an alkyl radical;

$(4-m-n)H—X—Ar—Y_c)$ [5]

wherein X represents an oxygen or sulphur atom, Ar represents an aromatic ring, Y represents a hydrocarbon radical, a silyl radical, a halogen atom, a halogenated hydrocarbon radical, a nitrogen-containing organic radical, an oxygen-containing organic radical or a sulphur-containing organic radical, and c is an integer of 1–5;

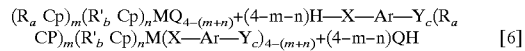

$(R_a\ Cp)_m(R'_b\ Cp)_nMQ_{4-(m+n)}+(4-m-n)H—X—Ar—Y_c(R_a\ CP)_m(R'_b\ Cp)_nM(X—Ar—Y_c)_{4-(m+n)}+(4-m-n)QH$ [6]

wherein $R_a$ Cp and $R'_b$Cp, M, Q, X, Ar, Y, a, b, m, n and c each has the same meaning as in the general formulae [4]–[5].

In the reaction equation [6], the reaction temperature is −78° C. to 100 ° C., preferably 0° C. to 80° C., and the reaction time is 0.1 to 50 hrs, preferably 0.5 to 30 hrs. As a solvent hydrocarbon such as benzene, toluene or xylene; ethers such as tetrahydrofuran and diethylether; and a halogenated hydrocarbon such as chloroform and dichloromethane. These reaction solvents may be used generally in an amount within 10 to 500 times of the compound of the general formula [3] or [4].

The reaction of the equation [6] proceeds in general quantitatively so that the compound of the general formula [4] and [5] may be reacted each other in a stoichiometrically required amount. When the solvent is distilled off in vacuum from the reaction solution after the reaction, the final transition metal compound is obtained. Of course, after the solvent is distilled off in vacuum from the solution after the reaction of equation [6], the final compound may be further purified by a process such as recrystallization.

As other process for synthesizing the transition metal compound according to the present invention, there may be used a process in which the compound of the general formula [3] is reacted directly with an alkali metal salt of the compound of the general formula [5] and a process, which is described for example in Journal of Organometallic Chemistry 485 (1995) 153–160, i.e. a process in which the compound of the formula [3] is reacted directly with the compound of the formula (5) in the presence of base compound such as an amine.

On the other hand, the transition metal compound represented by the general formula [2] may be synthesized in the same manner as in the process for synthesizing the compound of the general formula [1].

The catalyst for the polymerization of olefins according to the present invention is characterized by using as co-catalyst an organic aluminum oxy compound or a cation generator and, if necessary, an organic aluminum compound in combination of said transition metal compound.

The organic aluminum oxy compound may be selected from the linear alkylaluminoxanes of the general formula [7] and the cyclic alkylaluminoxanes of the general formula [8].

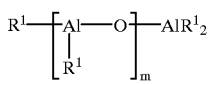  [7]

Wherein $R^1$ represents a hydrogen atom, a halogen atom or an alkyl radical having 1 to 10 carbon atoms and m is an integer of 2 to 40.

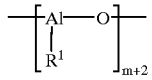  [8]

Wherein $R^1$ and m each has the same meaning in the general formula [7].

As to $R^1$ in the general formulae [7] and [8], the halogen atom is a chlorine or bromine atom and the alkyl radical having 1–10 carbon atoms is methyl, ethyl, iso-butyl and the like. The compound of the formulae [7] and [8] may be contain different $R^1$ radical therein. Preferably, the compound has above all methyl or methyl and other radicals. The number of repeating unit, m, is selected from within the range of 2–40, preferably 5–20.

Various known processes may be used for the synthesis of the alkylalminoxanes of the formulae [7] and [8]. For example, the compounds may be synthesized by a process in which a trialkyl aluminum is dissolved in a hydrocarbon solvent and hydrolyzed by adding gradually an equivalent amount of water to the trialkyl aluminum in the solution; a process in which a hydrate of copper sulfate or aluminum sulfate is suspended in a hydrocarbon solvent and a trialkyl aluminum in an amount of 1–3 times equivalent to the crystal water of said hydrate in the suspension is contacted to the hydrate to hydrolyze gradually the trialkylaluminum; or a process in which the adsorption water of undehydrated silica gel suspended in a hydrocarbon solvent is contacted to a trialkyl aluminum in an amount of 1 to 3 times equivalent to said adsorption water to hydrolyze gradually the trialkyl aluminum.

On the other hand, as the cation generator among the co-catalyst, there are mentioned those of the neutral and ion-pair type; those of neutral type include, for example, the organic boron compounds represented by the general formula [9]

  [9]

wherein $R^2$ represents a hydrogen atom, a hydrocarbon radical having 1 to 20 carbon atoms or a halogen atom.

Preferably, the compounds of the general formula [9] are especially those, in which a hydrocarbon radical to be bonded to the boron atom. The three $R^2$ radical may be same or different and except for hydrocarbon radicals, a part of three $R^2$ may be substituted by a hydrogen or halogen atom.

Examples of $R^2$ include an alkyl radical such as methyl, ethyl, n-propyl, iso-butyl and n-octyl; or an aryl radical such as phenyl and tolyl.

Concrete examples of the organic boron compounds of the formula [9] include triphenylborane, tris (pentafluorophenyl)borane, tris(2,3,4,5-tetrafluorophenyl) borane, tris(2,4,6-trifluorophenyl)borane, tris(2,3-difluorophenyl)borane, tris(2-fluorophenyl)borane, tris[3,5-bis(trifluoromethyl)phenyl]borane, tris[4-(trifluoromethyl) phenyl]borane, trimethylborane, triethylborane, tris (trifluoromethyl)borane, diphenylfluoroborane, bis (pentafluorophenyl)chloroborane. Of these, prefered ones are tris(pentafluorophenyl]borane and tris[3,5-bis (trifluoromethyl)phenyl]borane.

The ion pair type cation generators are compounds of the formula [10].

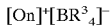  [10]

wherein $[On]^+$ is a metal cation of group 1B, 2B, or 8, carbenium ion, silicenium ion, oxonium ion, sulfonium ion, ammonium ion or phosphonium ion, and $R^3$ is a hydorocarbon radical having 1 to 20 carbon atoms, respectively.

Concrete examples of the cation generators of the formula [10] include salts of tetrakis(pentafluorophenyl)borate, such as ferrocenium tetrakis(pentafluorophenyl)borate, silver (I) tetrakis(pentafluorophenyl)borate, copper (I) tetrakis (pentafluorophenyl)borate, marcury (II) bis[tetrakis (pentafluorophenyl)]borate, palladium (II) bis[tetrakis (pentafluorophenyl)]borate, platinum (II) bis[tetrakis (pentafluorophenyl)]borate, diphenylhydorocarbenium tetrakis(pentafluorophenyl)borate, triphenylcarbenium tetrakis(pentafluorophenyl)borate, tricyclohexylcarbenium tetrakis(pentafluorophenyl)borate, triphenylsilicenium tetrakis(pentafluorophenyl)borate, triethyloxonium tetrakis (pentafluorophenyl)borate, triethylsulfonium tetrakis (pentafluorophenyl)borate, diethylanilinium tetrakis (pentafluorophenyl)borate, trimethylammonium tetrakis (pentafluorophenyl)borate, triethylammonium tetrakis (pentafluorophenyl)borate, tetra-n-butylammonium tetrakis (pentafluorophenyl)borate, triphenylphosphonium tetrakis (pentafluorophenyl)borate.

In the practice of the present invention, the organic aluminum compound represented by the general formula [11] may be co-existed, if necessary, in order to stabilize the catalyst or in order to stabilize the organic aluminum oxy compound or cation generator as the above-mentioned co-catalyst and reduce the amount to be used.

  [11]

wherein $R^4$ represents a hydrogen atom, an alkyl radical having 1–10 carbon atoms or a halogen atom, proviso that all $R^4$ radicals are not hydrogen or halogen atoms.

$R^4$ as an alkyl radical having 1–10 carbon atoms is, for example, methyl, ethyl, iso-butyl or octyl radical and as a halogen atom is, for example, a chlorine or bromine atom. Further, the radical $R^4$ of the compounds represented by the general formula [11] may be same or different.

As the compounds of the formula [11], there may be mentioned, for instance, trimethylaluminum, triethylaluminum, triisobutylaluminum, trihexylaluminum, trioctylaluminum, diisobutylaluminum hydride, diethtylaluminum chloride, ethylaluminum sesquichloride.

In the practice of the polymerization of olefines in the present invention, the catalyst for the polymerization may be prepared by adding the transition metal compound according to the present invention as catalyst component and an organic aluminum oxy compound or cation generator as a co-catalyst, and if necessary, an organic aluminum compound to an inert hydrocarbon solvent or an olefin medium to be polymerized. Then, the addition order of each component may be selected optionally, the transition metal compound and co-catalyst may be used after mixing and contacting them for a certain time before the polymerization previously, or each component may be also added respectively to the polymerization system.

The transition metal compound according to the present invention for the polymerization of olefins is used in general in a catalyst concentration within the range of $10^{-8}$–$18$–$10^{-1}$ mol/liter, preferably $10^{-7}$–$10^{-3}$ mol/liter. On the other hand, the organic aluminum oxy compound as co-catalyst is used in general within the range of 10–$10^5$, preferably 50 to $5\times10^3$ of the ratio of aluminum atom/transition metal atom. The cation generator as co-catalyst is used in general within the range of 0.5 to 10, preferably 1 to 5 of the mol ratio of cation generator/transition metal compound. The organic aluminum compound of the general formula (11) is used in general within the range of 1 to $10^5$, preferably 10 to $10^4$ of the ratio of aluminum atom/transition metal atom.

The polymerization according to the present invention can be carried out by means of every polymerization process such as the slurry, solution or gas-phase polymerization. In the slurry or gas-phase polymerization, either the catalyst component of the transition metal compound or the co-catalyst or both of them may be deposited on a support for use. Examples of support include, for example, an inorganic oxide support such as silica, alumina or silica-alumina; an inorganic support such as magnesium chloride; and an organic support such as polyethylene and polypropylene. The method for supporting on a support is not critical and any known method may be used. The catalyst supported on a support may be subjected to the so-called prepolymerization treatment, in which a relatively small amount of olefin is previously polymerized in the polymerization of olefines, where the amount of olefin polymer to be produced is preferably up to 0.05 to 500 g, preferably up to 0.1 to 100 g per g of the carried catalyst. A process in which either the catalyst component or the co-catalyst or both of them is supported on a support and used, or a process in which either the catalyst component or the co-catalyst or both of them is used after the prepolymerization, is a available especially for the slurry or gas-phase polymerization because the particle shape and bulk density of the polymer produced are improved and the like.

Olefins to be used in the process according to the present invention include not only α-olefins but also those other than α-olefins for example, linear diolefins, cyclic olefins, cyclic polyenes, aromatic vinyl compounds, or the like.

As alpha-olefins, those having 2 to 20 carbon atoms are particularly mentioned. For instance, ethylene, propylene, 1-butene, 3-methyl-1-butene, 1-pentene, 1-hexene, 4-methyl-1-pentene, 3-methyl-1-pentene, 1-octene, 1-decene, 1-dodecene, 1-tetradecene, 1-hexadecene, 1-octadecene, 1-tetradecene, 1-hexadecene, 1-octadecene, 1-eicocene, vinylcyclohexane, vinylcyclohexene, trimethylvinylsilane may be mentioned.

Linear diolefins are, particularly, those having 4 to 20 carbon atoms. For instance, non-conjugated dienes, such as 1,4-pentadiene, 1,4-hexadiene, 1,5-hexadiene, 4-methyl-1,4-hexadiene, 5-methyl-1,4-hexadiene, 5-methyl-1,5-heptadiene, 1,7-octadiene, 7-methyl-1,6-octadiene and: 1,9-decanediene, or conjugated dienes, such as butadiene, isoprene, chloroprene, 1,3-pentadiene and 1,3-hexadiene may be mentioned.

Cyclic olefins are, particularly, those having 4 to 40 carbon atoms. For instance, cyclobutene, cyclopentene, cyclohexene, cycloheptene, cyclooctene, 2-norbornene, 5-methyl-2-norbornene, 5-ethyl-2-norbornene, 5-chloro-2-norbornene, 5-methoxy-2-norbornene, 5,6-dicarboxylnorbornene anhydrate, tetracyclododecene, 5-phenylnorbornene may be mentioned.

Cyclic polyenes are, particularly, those having 5 to 40 carbon atoms. For instance, cyclopentadiene, dicyclopentadiene, norbornadiene, 5-vinyl-2-norbornene, 5-ethylidene-2-norbornene, cyclooctatriene may be mentioned. As aromatic vinyl compounds, for instance, styrene, alpha-methylstyrene, divinylbenzene are usable.

These olefins may be homopolymerized and two or more than two olefins may be copolymerized.

In the present invention, an inert hydrocarbon solvent or the olefin itself to be polymerized may be used for carring out the solution or slurry polymerization. As inert hydrocarbon solvents, there may be used, for example, an aliphatic hydrocarbon such as butane, isobutane, pentane, hexane, octane, an alicyclic hydrocarbon such as cyclopentane, methylcyclopentane or cyclohezane; an aromatic hydrocarbon such as benzene, toluene or zylene; and a petroleum fraction such as naphtha, kerosene or light oil.

The polymerization temperature in the practice of the polymerization of the present invention is in general within the range of −20 to 100° C., preferably 20 to 90° C. in the slurry polymerization, and in general within the range of 0 to 120° C., preferably 20 to 100° C. in the gas-phase polymerization; it is in general within the range of 0 to 300° C., preferably 100 to 250° C. in the solution polymerization. The polymerization pressure is not critical, but is used in general within the range from a atomspheric pressure to 100 kg/cm$^2$.

The polymerization according to the present invention may be carried out in a batch, semi-continuous or continuous method and in two or more than two steps of different reaction condition. The molecular weight (weight average molecular weight) of olefin polymer obtained by using the catalyst according to the present invention is in general 1,000 to 10,000,000, especially 5,000 to 5,000,000. The molecular weight of olefin polymer obtained may be controlled by the presence of hydrogen in the polymerization reaction system or the change of polymerization temperature.

BEST MODE FOR CARRYING OUT THE INVENTION

Figure 1:
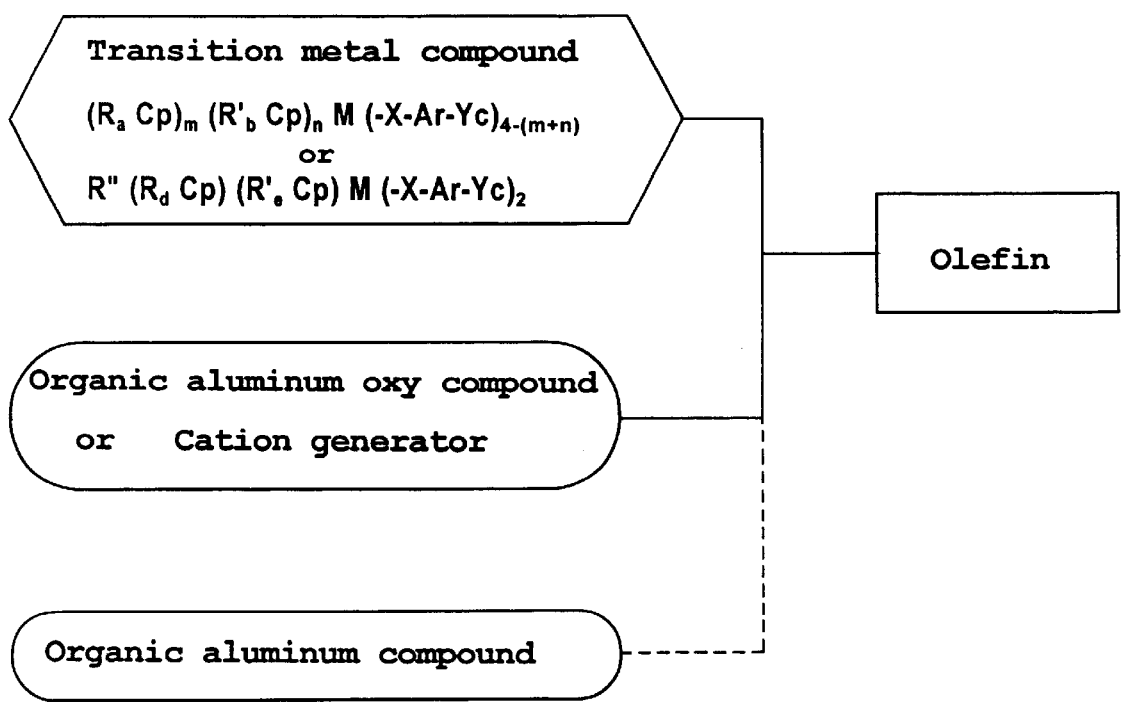
FIG. 1 is a flow chart illustrating the preparation steps of the catalyst according to the present invention.

The present invention will be explained in detail hereinafter by examples, by which the present invention is not limited thereto only.

In the synthesis of the transition metal compounds in the following examples, the transition metal compounds represented by the general formula [4] used as the starting material are those, which are available commercially or are prepared by the method described in literature (for example, Journal of American Chemical Society 95 (1973) 6263–6267).

The aromatic hydroxy or thiol compounds represented by the general formula [5] as another starting material are those, which are available commercially.

All preparative reactions were carried out under an argon atmosphere using a standard Schlenk technique.

The yield is calculated based on the transition metal compound as starting material and shown in % (by weight).

The resulting transition metal compound was identified by means of $^1$H-NMR spectroscopy (δ (unit: ppm)) and the elementary analysis (unit: % by weight).

The dilution of catalyst component and the operation of polymerization and the like were carried out under argon atmosphere. The comonomer content in the copolymer was determined by means of $^{13}$C-NMR spectroscopy.

I. Synthesis of Catalyst Component

EXAMPLE 1

Synthesis of Catalyst Component (a)-1
(Dicyclopentadienylbis(2-methylphenoxy)
zirconium)

To a 50 ml Schlenk tube having been sufficiently exchanged by argon, 10 ml of toluene solution containing 106.0 mg of dicyclopentadienyldimethyl zirconium and 90.6 mg of orthocresol were added and the resultant mixture was stirred at room temperature for 1 hr. After the completion of reaction, toluene was distilled off under reduced pressure to yield a transition metal compound of white solid (catalyst component (a)-1). The yield amount of the catalyst component (a)-1 was 176.7 mg corresponding to 99% yield.

The results of the $^1$H-NMR spectoroscopy (measured in C$_6$D$_6$) and the elementary analysis of the product were as follows:

$^1$H-NMR spectral data: δ 2.23(s, 6H), 5.94 (s, 10H), 6.67 (d, 2H, J=7.6 Hz), 6.89(d, 2H, J=7.2 Hz) 7.18(d, 2H, J=7.4 Hz), 7.19(d, 2H, J=7.4 Hz), elementary analysis: C 66.02, H 5.78, Zr 20.65.

By the results as mentioned above, the catalyst component (a)-1 was confirmed as dicyclopentadienylbis(2-methylphenoxy)zirconium.

EXAMPLES 2 TO 68

Synthesis of Catalyst Components (a)-2 to (a)-68

The same reaction as well as treatment after the reaction was carried out as in Example 1 except that the phenol compound to be reacted with dicyclopentadienyldimethyl zirconium was exchanged from orthocresol to the substituted phenol compounds as shown in Tables 1 to 5 and the amount of each starting material used was shown in Tables 1 to 5. The resulting transition metal compounds were shown as catalyst component (a)-2 to (a)-68 respectively. The yield amount, yield and appearance of each catalyst component are summarized in Tables 1 to 5. Each product was confirmed as the final transition metal compound by the results of elementary analysis and $^1$H-NMR spectoroscopy. The results are summarized in Tables 6 to 13.

TABLE 1

| Example No. | Catalyst component | Cp$_2$ZrMe$_2$ (used amount) (mg) | Substituted phenol compound | Usage (mg) | Yield amount (%) | Yield (%) | Appearance |
|---|---|---|---|---|---|---|---|
| Ex. 1 | (a)-1 | 106.0 | o-cresol | 90.6 | 181.0 | 99 | white solid |
| Ex. 2 | (a)-2 | 118.9 | m-cresol | 101.7 | 154.5 | 75 | colorless crystal |
| Ex. 3 | (a)-3 | 111.8 | p-cresol | 95.6 | 132.1 | 69 | colorless crystal |
| Ex. 4 | (a)-4 | 102.9 | 2-methoxyphenol | 108.0 | 188.0 | 99 | colorless oil |
| Ex. 5 | (a)-5 | 97.3 | 3-methoxyphenol | 95.3 | 181.4 | 100 | yellow oil |
| Ex. 6 | (a)-6 | 89.2 | 4-methoxyphenol | 87.4 | 161.3 | 99 | white solid |
| Ex. 7 | (a)-7 | 147.3 | 2-trifluoromethyl-phenol | 188.7 | 253.3 | 80 | colorless crystal |
| Ex. 8 | (a)-8 | 105.6 | 3-trifluoromethyl-phenol | 125.0 | 228.2 | 99 | white solid |
| Ex. 9 | (a)-9 | 131.5 | 4-trifluoromethyl-phenol | 168.3 | 189.2 | 67 | colorless crystal |
| Ex. 10 | (a)-10 | 97.5 | 2-cyanophenol | 92.4 | 175.8 | 99 | red solid |
| Ex. 11 | (a)-11 | 116.3 | 3-cyanophenol | 110.2 | 195.6 | 93 | colorless crystal |
| Ex. 12 | (a)-12 | 112.5 | 4-cyanophenol | 106.5 | 206.6 | 100 | white solid |
| Ex. 13 | (a)-13 | 132.4 | 2-nitrophenol | 146.5 | 200.1 | 76 | yellow crystal |
| Ex. 14 | (a)-14 | 116.1 | 3-nitrophenol | 128.4 | 168.3 | 73 | yellow crystal |
| Ex. 15 | (a)-15 | 100.4 | 4-nitrophenol | 110.1 | 188.5 | 95 | yellow crystal |
| Ex. 16 | (a)-16 | 148.2 | 2-chlorophenol | 151.4 | 277.9 | 99 | colorless oil |

TABLE 2

| Example No. | Catalyst component | Cp$_2$ZrMe$_2$ (used amount) (mg) | Substituted phenol compound | Usage (mg) | Yield amount (mg) | Yield (%) | Appearance |
| --- | --- | --- | --- | --- | --- | --- | --- |
| Ex. 17 | (a)-17 | 110.9 | 3-chlorophenol | 113.4 | 177.0 | 84 | colorless crystal |
| Ex. 18 | (a)-18 | 116.2 | 4-chlorophenol | 119.0 | 220.2 | 100 | white solid |
| Ex. 19 | (a)-19 | 207.1 | 2-fluorophenol | 183.4 | 359.5 | 99 | white solid |
| Ex. 20 | (a)-20 | 212.2 | 3-fluorophenol | 187.9 | 295.5 | 79 | colorless crystal |
| Ex. 21 | (a)-21 | 209.7 | 4-fluorophenol | 185.6 | 374.4 | 100 | white solid |
| Ex. 22 | (a)-22 | 83.3 | 2-bromophenol | 113.8 | 191.6 | 100 | colorless oil |
| Ex. 23 | (a)-23 | 80.6 | 3-bromophenol | 110.0 | 187.0 | 100 | white solid |
| Ex. 24 | (a)-24 | 84.7 | 4-bromophenol | 115.9 | 191.4 | 100 | colorless oil |
| Ex. 25 | (a)-25 | 53.6 | 2-iodophenol | 93.3 | 142.5 | 100 | yellow oil |
| Ex. 26 | (a)-26 | 58.8 | 3-iodophenol | 102.1 | 155.9 | 100 | white solid |
| Ex. 27 | (a)-27 | 62.1 | 4-iodophenol | 107.8 | 162.8 | 100 | colorless oil |
| Ex. 28 | (a)-28 | 73.8 | 2-ethylphenol | 71.3 | 138.9 | 100 | yellow oil |
| Ex. 29 | (a)-29 | 73.6 | 3-ethylphenol | 71.1 | 135.5 | 100 | colorless oil |
| Ex. 30 | (a)-30 | 76.2 | 4-ethylphenol | 73.5 | 138.5 | 99 | colorless oil |
| Ex. 31 | (a)-31 | 70.1 | 2-isopropylphenol | 75.4 | 136.4 | 100 | colorless oil |
| Ex. 32 | (a)-32 | 76.6 | 3-isopropylphenol | 82.5 | 147.7 | 99 | colorless oil |

TABLE 3

| Example No. | Catalyst component | Cp$_2$ZrMe$_2$ (used amount) (MG) | Substituted phenol compound | Usage (mg) | Yield amount (mg) | Yield (%) | Appearance |
| --- | --- | --- | --- | --- | --- | --- | --- |
| Ex. 33 | (a)-33 | 76.5 | 4-isopropylphenol | 82.3 | 146.4 | 99 | colorless oil |
| Ex. 34 | (a)-34 | 70.6 | 2-tert-butylphenol | 83.8 | 149.1 | 100 | colorless oil |
| Ex. 35 | (a)-35 | 68.7 | 3-tert-butylphenol | 81.4 | 142.7 | 100 | colorless oil |
| Ex. 36 | (a)-36 | 68.4 | 4-tert-butlphenol | 81.1 | 140.9 | 100 | white solid |
| Ex. 37 | (a)-37 | 104.9 | 2,3-difluorophenol | 109.0 | 206.0 | 100 | white solid |
| Ex. 38 | (a)-38 | 134.0 | 2,4-difluorophenol | 137.6 | 251.2 | 99 | white solid |
| Ex. 39 | (a)-39 | 90.0 | 2,5-difluorophenol | 93.6 | 170.0 | 99 | white solid |
| Ex. 40 | (a)-40 | 164.7 | 2,6-difluorophenol | 169.4 | 309.0 | 99 | white solid |
| Ex. 41 | (a)-41 | 89.6 | 3,4-difluorophenol | 93.0 | 169.7 | 100 | white solid |
| Ex. 42 | (a)-42 | 101.3 | 3,5-difluorophenol | 105.0 | 190.1 | 99 | white solid |
| Ex. 43 | (a)-43 | 83.2 | 2,3,4-trifluoro-phenol | 96.6 | 134.5 | 80 | colorless crystal |
| Ex. 44 | (a)-44 | 86.2 | 2,3,6-trifluoro-phenol | 101.1 | 71.4 | 41 | colorless crystal |
| Ex. 45 | (a)-45 | 97.5 | 2,4,5-trifluoro-phenol | 115.0 | 205.3 | 100 | white solid |
| Ex. 46 | (a)-46 | 100.6 | 2,4,6-trifluoro-phenol | 118.1 | 205.1 | 100 | white solid |

TABLE 3-continued

| Example No. | Catalyst component | Cp$_2$ZrMe$_2$ (used amount) (MG) | Substituted phenol compound | Usage (mg) | Yield amount (mg) | Yield (%) | Appearance |
|---|---|---|---|---|---|---|---|
| Ex. 47 | (a)-47 | 233.8 | 2,3,5,6-tetrafluorophenol | 306.9 | 451.5 | 89 | colorless crystal |
| Ex. 48 | (a)-48 | 304.7 | pentafluorophenol | 441.7 | 387.3 | 55 | colorless crystal |

TABLE 4

| Example No. | Catalyst component | Cp$_2$ZrMe$_2$ (used amount) (mg) | Substituted phenol compound | Usage (mg) | Yield amount (mg) | Yield (%) | Appearance |
|---|---|---|---|---|---|---|---|
| Ex. 49 | (a)-49 | 65.1 | 2-phenylphenol | 87.5 | 105.0 | 73 | white crystal |
| Ex. 50 | (a)-50 | 73.4 | 3-phenylphenol | 98.7 | 166.2 | 100 | yellow oil |
| Ex. 51 | (a)-51 | 64.1 | 4-phenylphenol | 86.2 | 98.2 | 69 | white crystal |
| Ex. 52 | (a)-52 | 90.5 | 2-hydroxyacetophenone | 97.2 | 174.7 | 99 | yellow oil |
| Ex. 53 | (a)-53 | 100.7 | 3-hydroxyacetophenone | 108.1 | 200.7 | 100 | colorless oil |
| Ex. 54 | (a)-54 | 89.2 | 4-hydroxyacetophenone | 95.8 | 74.4 | 43 | white crystal |
| Ex. 55 | (a)-55 | 72.3 | methyl salicylate | 87.0 | 151.9 | 100 | yellow oil |
| Ex. 56 | (a)-56 | 69.1 | methyl 3-hydroxybenzoate | 83.1 | 143.5 | 100 | colorless oil |
| Ex. 57 | (a)-57 | 69.0 | methyl 4-hydroxybenzoate | 83.1 | 76.3 | 53 | white crystal |
| Ex. 58 | (a)-58 | 121.5 | 2,4-dichlorophenol | 156.5 | 154.5 | 59 | white crystal |
| Ex. 59 | (a)-59 | 101.4 | 2,4-dimethylphenol | 98.0 | 188.6 | 100 | colorless oil |
| Ex. 60 | (a)-60 | 74.5 | 2-chloro-4-trifluoromethylphenol | 123.6 | 191.4 | 100 | colorless oil |
| Ex. 61 | (a)-61 | 62.5 | 2-chloro-4-fluorophenol | 74.5 | 125.8 | 99 | white crystal |
| Ex. 62 | (a)-62 | 52.2 | 2-chloro-4-nitrophenol | 72.0 | 95.7 | 82 | yellow crystal |
| Ex. 63 | (a)-63 | 53.6 | 2-fluoro-4-nitrophenol | 66.8 | 98.4 | 87 | yellow crystal |
| Ex. 64 | (a)-64 | 66.9 | 2-methyl-4-fluorophenol | 69.9 | 64.7 | 52 | white crystal |

TABLE 5

| Example No. | Catalyst component | Cp$_2$ZrMe$_2$ (used amount) (mg) | Substituted phenol compound | Usage (mg) | Yield amount (mg) | Yield (%) | Appearance |
|---|---|---|---|---|---|---|---|
| Ex. 65 | (a)-65 | 79.3 | 1-naphthol | 89.8 | 100.1 | 63 | white crystal |
| Ex. 66 | (a)-66 | 76.2 | 2-naphthol | 86.7 | 73.3 | 48 | white crystal |
| Ex. 67 | (a)-67 | 90.8 | 2-fluorothiophenol | 92.0 | 110.0 | 64 | yellow crystal |
| Ex. 68 | (a)-68 | 74.0 | 2-chlorothiophenol | 84.5 | 148.5 | 100 | yellow solid |

TABLE 6

| Catalyst component | Elementary analysis (wt %) C | H | Zr | $^1$H-NMR spectral data ($\delta$: ppm) |
|---|---|---|---|---|
| (a)-1 | 66.02 | 5.78 | 20.65 | $\delta$ 2.23(s, 6H), 5.94(s, 10H), 6.67(d, 2H, J = 7.6 Hz), 6.89 (d, 2H, J = 7.2 Hz), 7.18(d, 2H, J = 7.4 Hz), 7.19(d, 2H, J = 7.4 Hz) |
| (a)-2 | 66.13 | 5.62 | 20.78 | $\delta$ 2.26(s, 6H), 6.00(s, 10H), 6.65(d, 2H, J = 8.1 Hz), 6.73 (s, 2H), 6.74(d, 2H, J = 8.5 Hz), 7.21(d, 2H, J = 7.7 Hz) |
| (a)-3 | 66.10 | 5.65 | 20.87 | $\delta$ 2.25(s, 6H), 6.00(s, 10H), 6.75(d, 4H, J = 8.3 Hz), 7.08 (d, 4H, J = 8.3 Hz) |
| (a)-4 | 61.33 | 5.43 | 19.39 | $\delta$ 3.44(s, 6H), 6.13(s, 10H), 6.74(d, 2H, J = 7.9 Hz), 6.82–6.86(m, 2H), 6.95–6.98(m, 4H) |
| (a)-5 | 61.58 | 5.31 | 19.33 | $\delta$ 3.45(s, 6H), 5.99(s, 10H), 6.45–6.59(m, 6H), 7.17 (s, 2H) |

TABLE 7

| Catalyst component | Elementary analysis (wt %) C | H | Zr | $^1$H-NMR spectral data ($\delta$: ppm) |
|---|---|---|---|---|
| (a)-6 | 61.43 | 5.44 | 19.41 | $\delta$ 3.45(s, 6H), 6.02(s, 10H), 6.73(d, 4H, J = 8.9Hz), 6.89(d, 4H, J = 8.9 Hz) |
| (a)-7 | 53.00 | 3.42 | 16.65 | $\delta$ 6.02(s, 10H), 6.60(t, 2H, J = 7.6 Hz), 6.70(d, 2H, J = 8.2 Hz), 7.08(t, 2H, J = 7.8 Hz), 7.47(dd, 2H, J = 7.8&1.3Hz) |
| (a)-8 | 52.87 | 3.56 | 16.85 | $\delta$ 5.79(s, 10H), 6.68(d, 2H, J = 7.8 Hz), 7.03(t, 2H, J = 7.8 Hz), 7.08(s, 2H), 7.09(d, 2H, J = 7.8 Hz) |
| (a)-9 | 52.91 | 3.68 | 16.50 | $\delta$ 5.82(s, 10H), 6.50(d, 4H, J = 8.5 Hz), 7.50(d, 4H, J = 8.5 Hz) |
| (a)-10 | 62.80 | 4.08 | 19.71 | $\delta$ 6.12(s, 10H), 6.43(dt, 2H, J= 7.5&1.0 Hz), 6.73(d, 2H, J = 8.3 Hz), 7.05(ddd, 2H, J = 8.3, 7.5&1.7 Hz), 7.14(dd, 2H, J = 7.5&1.7 Hz) |
| (a)-11 | 62.87 | 4.05 | 19.87 | $\delta$ 5.72(s, 10H), 6.54–6.58(m, 2H), 6.73(s, 2H), 6.79–6.83(m, 4H) |
| (a)-12 | 62.73 | 4.20 | 19.68 | $\delta$ 5.80(s, 10H), 6.30(d, 4H, J= 8.4 Hz), 7.23(d,4H, J = 8.4 Hz) |
| (a)-13 | 53.03 | 3.87 | 18.12 | $\delta$ 5.97(s, 10H), 6.41(ddd, 2H, J = 8.3, 7.5,&1.2 Hz), 6.70(dd, 2H, J = 8.3&1.2 Hz), 6.99(ddd, 2H, J = 8.2, 1.5&1.7 Hz), 7.69(dd, 2H, J = 8.2&1.7 Hz) |
| (a)-14 | 52.98 | 3.98 | 18.19 | $\delta$ 5.77(s, 10H), 6.70(ddd, 2H, J = 7.0, 2.3&0.8 Hz), 6.87 (t, 2H, J = 8.1 Hz), 7.52(t, 2H, J = 2.3 Hz), 7.67(ddd, 2H, J = 8.1, 2.3&1.0 Hz) |

TABLE 8

| Catalyst component | Elementary analysis (wt %) C | H | Zr | $^1$H-NMR spectral data ($\delta$: ppm) |
|---|---|---|---|---|
| (a)-15 | 53.08 | 3.72 | 18.29 | $\delta$ 5.73(s, 10H), 6.22(d, 4H, J = 9.0 Hz), 8.12(d, 4H, J = 9.0 Hz) |
| (a)-16 | 55.30 | 4.00 | 19.01 | $\delta$ 6.02(s, 10H), 6.60(dt, 2H, J = 7.6&1.6 Hz), 6.85(dd, 2H, J = 8.1&1.6 Hz), 6.99(ddd, 2H, J = 8.1, 7.6&1.6 Hz), 7.14(dd, 2H, J = 7.9&1.6 Hz) |
| (a)-17 | 55.32 | 3.99 | 19.09 | $\delta$ 5.80(s, 10H), 6.49(dt, 2H, J = 7.7&1.7 Hz), 6.83(t, 2H, J = 2.1 Hz), 6.88–6.95(m, 4H) |
| (a)-18 | 55.24 | 4.11 | 19.00 | $\delta$ 5.85(s, 10H), 6.44(d, 4H, J = 8.7 Hz), 7.19(d, 4H, J = 8.7 Hz) |
| (a)-19 | 59.06 | 4.27 | 20.21 | $\delta$ 6.01(s, 10H), 6.62(m, 2H), 6.90(m, 4H), 7.02(m, 2H) |
| (a)-20 | 59.23 | 4.11 | 20.43 | $\delta$ 5.86(s, 10H), 6.43(ddd, 2H, J = 8.2, 2.3&0.8 Hz), 6.5 6.50(dt, 2H, J = 10.9&2.3 Hz), 6.43(tdd, 2H, J = 8.2, 2.4&0.8 Hz), 6.99(dt, 2H, J = 8.1&7.3 Hz) |
| (a)-21 | 59.40 | 4.16 | 20.31 | $\delta$ 5.92(s, 10H), 6.48(dd, 4H, J = 8.9&4.6 Hz), 6.91(dd, 4H, J = 8.9&8.8 Hz) |

TABLE 8-continued

| Catalyst component | Elementary analysis (wt %) | | | $^1$H-NMR spectral data |
|---|---|---|---|---|
| | C | H | Zr | (δ : p p m) |
| (a)-22 | 46.56 | 3.46 | 16.04 | δ 6.05(s, 10H), 6.53(ddd, 2H, J = 8.0, 7.2&1.6 Hz), 6.84 (dd, 2H, J = 8.0&1.6 Hz), 7.00(ddd, 2H, J = 8.0, 7.2&1.6 Hz), 7.52(dd, 2h, J = 8.0&1.6 Hz) |
| (a)-23 | 46.36 | 3.31 | 16.00 | δ 5.79(s, 10H), 6.51(ddd, 2H, J = 8.0, 2.1&1.1 Hz), 6.86 (t, 2H, J = 8.0 Hz), 7.01(t, 2H, J = 2.1 Hz), 7.03(ddd, 2H, J = 8.0, 2.1&1.1 Hz) |

TABLE 9

| Catalyst component | Elementary analysis (wt %) | | | $^1$H-NMR spectral data |
|---|---|---|---|---|
| | C | H | Zr | (δ : p p m) |
| (a)-24 | 46.65 | 3.38 | 16.07 | δ 5.84(s, 10H), 6.38(d, 4H, J = 8.8 Hz), 7.33(d, 4H, J = 8.8 Hz) |
| (a)-25 | 39.88 | 2.96 | 13.69 | δ 6.10(s, 10H), 6.40(ddd, 2H, J = 7.8, 7.2&1.5 Hz), 6.80 (dd, 2H, J = 8.0&1.5 Hz), 7.03(ddd, 2H, J = 8.0, 7.2&1.6 Hz), 7.75(dd, 2H, J = 7.8&1.6 Hz) |
| (a)-26 | 39.92 | 3.06 | 13.69 | δ 5.78(s, 10H), 6.55(ddd, 2H, J = 8.0, 2.2&1.1 Hz), 6.72 (t, 2H, J = 8.0 Hz), 7.22(ddd, 2H, J = 8.0, 2.1&1.1 Hz), 7.24(t, 2H, J = 2.2 Hz) |
| (a)-27 | 40.02 | 2.89 | 13.70 | δ 5.83(s, 10H), 6.29(d, 4H, J = 8.7 Hz), 7.51(d, 4H, J = 8.7 Hz) |
| (a)-28 | 67.56 | 5.81 | 19.49 | δ 1.27(t, 6H, J = 7.6 Hz), 2.68(q, 4H, J = 7.6 Hz), 5.98(s, 10H), 6.65(dd, 2H, J = 7.7&1.1 Hz), 6.93(dt, 2H, J = 7.7, 7&1.1 Hz), 7.17–7.23(m, 4H) |
| (a)-29 | 67.20 | 6.19 | 19.84 | δ 1.22(t, 6H, J = 7.6 Hz), 2.59(q, 4H, J = 7.6 Hz), 6.02(s, 10H), 6.65–6.69(m, 2H), 6.76–6.80(m, 4H), 7.24(t, 2 H, J = 7.8 Hz) |
| (a)-30 | 67.22 | 6.08 | 19.96 | δ 1.21(t, 6H, J = 7.6 Hz), 2.58(quint, 4H, J = 7.6 Hz), 6.00(s, 10H), 6.79(d, 4H, J = 8.4 Hz), 7.12(d, 4H, J = 8.4 Hz) |
| (a)-31 | 68.31 | 6.69 | 18.41 | δ 1.32(d, 12H, J = 6.9 Hz), 3.44(quint, 2H, J = 6.9 Hz), 6.01(s, 10H), 6.61(dd, 2H, J = 7.8&1.2 Hz), 6.97(dt, 2H, J = 7.8, 7.8&1.2 Hz), 7.18(dt, 2H, J = 7.8, 7.8&1.8 Hz), 7.28(dd, 2H, J = 7.8&1.8 Hz) |

TABLE 10

| Catalyst component | Elementary analysis (wt %) | | | $^1$H-NMR spectral data |
|---|---|---|---|---|
| | C | H | Zr | (δ : p p m) |
| (a)-32 | 67.99 | 6.68 | 18.27 | δ 1.27(d, 12H, J = 6.9 Hz), 2.83(quint, 2H, J = 6.9 Hz), 6.03(s, 10H), 6.66(ddd, 2H, J = 7.8, 2.1&1.0 Hz), 6.81(d, 2H, J = 7.8 Hz), 6.84(t, 2H, J = 2.1 Hz), 7.26(t, 2H, J = 7.8 Hz) |
| (a)-33 | 68.18 | 6.87 | 18.41 | δ 1.26(d, 12H, J = 6.9 Hz), 2.84(quint, 2H, J = 6.9 Hz), 6.00(s, 10H), 6.81(d, 4H, J = 8.5 Hz), 7.17(d, 4H, J = 8.5 Hz) |
| (a)-34 | 69.21 | 7.11 | 17.36 | δ 1.50(s, 18H), 6.11(s, 10H), 6.77(dd, 2H, J = 7.8&1.4 Hz), 6.88(dt, 2H, J = 7.8, 7.8&1.4 Hz), 7.07(dt, 2H, J = 7.8, 7.8&1.7 Hz), 7.34(dd, 2H, J = 7.8&1.7 Hz) |
| (a)-35 | 69.17 | 7.06 | 17.65 | δ 1.35(s, 18H), 6.04(s, 10H), 6.67(ddd, 2H, J = 7.9&2.1 &1.0 Hz), 6.98(ddd, 2H, J = 7.9, 2.1&1.0 Hz), 7.03(t, 2 H, J = 2.1 Hz), 7.28(t, 2H, J = 7.9 Hz) |
| (a)-36 | 69.09 | 7.24 | 17.46 | δ 1.34(s, 18H), 6.02(s, 10H), 6.82(d, 4H, J = 8.6 Hz), 7.35(d, 4H, J = 8.6 Hz) |
| (a)-37 | 55.08 | 3.26 | 19.00 | |
| (a)-38 | 55.03 | 3.31 | 18.99 | δ 5.94(s, 10H), 6.56–6.64(m, 4H), 6.70–6.77(m, 2H) |
| (a)-39 | 55.19 | 3.38 | 19.14 | |

TABLE 10-continued

| Catalyst component | Elementary analysis (wt %) | | | $^1$H-NMR spectral data ($\delta$ : p p m) |
|---|---|---|---|---|
| | C | H | Zr | |
| (a)-40 | 54.99 | 3.53 | 18.92 | |
| (a)-41 | 54.91 | 3.39 | 18.97 | |
| (a)-42 | 54.90 | 3.44 | 19.03 | |

TABLE 11

| Catalyst component | Elementary analysis (wt %) | | | $^1$H-NMR spectral data ($\delta$ : p p m) |
|---|---|---|---|---|
| | C | H | Zr | |
| (a)-43 | 51.03 | 2.99 | 17.59 | |
| (a)-44 | 51.19 | 2.86 | 17.55 | |
| (a)-45 | 51.14 | 3.01 | 17.53 | |
| (a)-46 | 51.16 | 3.00 | 17.58 | |
| (a)-47 | 47.81 | 2.24 | 16.50 | $\delta$ 5.89(s, 10H), 6.07(m, 2H) |
| (a)-48 | 44.90 | 1.77 | 15.51 | $\delta$ 5.85(s, 10H) |
| (a)-49 | 72.88 | 5.13 | 16.21 | $\delta$ 5.70(s, 10H), 6.79(dd, 2H, J = 7.5&1.2 Hz), 6.92(dt, 2H, J = 7.5, 7.5&1.2 Hz), 7.13(dt, 2H, J = 7.5, 7.5&1.6 Hz), 7.21(dt, 2H, J = 7.6, 7.6&1.5 Hz), 7.23(t, 4H, J = 7.6 Hz), 7.35(dd, 2H, J = 7.5&1.6 Hz), 7.50(dd, 4H, J = 7.6&1.5 Hz) |
| (a)-50 | 72.99 | 5.32 | 16.18 | $\delta$ 5.99(s, 10H), 6.78(ddd, 2H, J = 7.8, 2.4&1.0 Hz), 7.11–7.25(m, 10H), 7.30(t, 2H, J = 7.8 Hz), 7.65(dd, 4H, J = 8.3&1.3 Hz) |
| (a)-51 | 73.06 | 4.97 | 16.09 | $\delta$ 6.01(s, 10H), 6.86(d, 4H, J = 8.6 Hz), 7.29(t, 4H, J = 7.7 Hz), 7.59(d, 4H, J = 8.6 Hz), 7.63(dd, 4H, J = 7.7&1.3 Hz) |
| (a)-52 | 63.46 | 4.88 | 18.25 | |
| (a)-53 | 63.32 | 5.02 | 18.36 | $\delta$ 2.25(s, 6H), 5.92(s, 10H), 6.92(ddd, 2H, J = 7.7, 2.4&1.0 Hz), 7.13(t, 2H, J = 7.7 Hz), 7.31(ddd, 2H, J = 7.7, 1.6&1.0 Hz), 7.59(dd, 2H, J = 2.4&1.6 Hz) |

TABLE 12

| Catalyst component | Elementary analysis (wt %) | | | $^1$H-NMR spectral data ($\delta$ : p p m) |
|---|---|---|---|---|
| | C | H | Zr | |
| (a)-54 | 63.39 | 5.07 | 18.40 | $\delta$ 2.26(s, 6H), 5.89(s, 10H), 6.62(d, 4H, J = 8.7 Hz), 8.01(d, 4H, 1 = 8.7 Hz) |
| (a)-55 | 59.43 | 4.87 | 17.31 | |
| (a)-56 | 61.00 | 4.69 | 16.34 | $\delta$ 3.56(s, 6H), 5.89(s, 10H), 6.89(ddd, 2H, J = 7.8, 2.4&1.0 Hz), 7.12(t, 2H, J = 7.8 Hz), 7.72(dd, 2H, J = 2.4&1.8 Hz), 7.83(ddd, 2H, J = 7.8, 1.8&1.0 Hz) |
| (a)-57 | 59.51 | 4.88 | 17.36 | $\delta$ 3.61(s, 6H), 5.83(s, 10H), 6.61(d, 4H, J = 8.6 Hz), 8.30(d, 4H, J = 8.6 Hz) |
| (a)-58 | 48.37 | 3.10 | 16.51 | $\delta$ 5.91(s, 10H), 6.50(d, 2H, J = 8.6 Hz), 6.96(dd, 2H, J = 8.6&2.5 Hz), 7.35(d, 2H, J = 2.5 Hz) |
| (a)-59 | 67.22 | 6.44 | 18.47 | $\delta$ 2.25(s, 6H), 2.28(s, 6H), 5.98(s, 5H), 6.09(s, 5H), 6.65(d, 2H, J = 8.5 Hz), 6.99(s, 2H), 7.01(d, 2H, J = 8.5 Hz) |
| (a)-60 | 47.02 | 2.89 | 14.54 | $\delta$ 5.87(s, 10H), 6.55(dd, 2H, J = 8.9&0.5 Hz), 7.26(ddd, 2H, J = 8.9, 2.3&0.5 Hz), 7.68(d, 2H, J = 2.3 Hz) |
| (a)-61 | 51.67 | 3.15 | 17.63 | $\delta$ 5.95(s, 10H), 6.53(dd, 2H, J = 8.9&5.3 Hz), 6.68(ddd, 2H, J = 8.9, 8.0&3.1 Hz), 7.06(dd, 2H, J = 8.0&3.1 Hz) |
| (a)-62 | 46.42 | 3.00 | 16.07 | $\delta$ 5.80(s, 10H), 6.28(d, 2H, J = 9.0 Hz), 7.86(dd, 2H, J = 9.0&2.8 Hz), 8.25(d, 2H, J = 2.8 Hz) |
| (a)-63 | 49.37 | 3.11 | 16.92 | $\delta$ 5.78(s, 10H), 6.34(t, 2H, J = 8.8 Hz), 7.82(ddd, 2H, J = 8.8, 2.5&1.1 Hz), 7.88(dd, 2H, J = 10.1&2.5 Hz) |

TABLE 13

| Catalyst component | Elementary analysis (wt %) | | | $^1$H-NMR spectral data (δ:ppm) |
|---|---|---|---|---|
| | C | H | Zr | |
| (a)-64 | 61.03 | 4.94 | 19.21 | δ 2.02(s, 6H), 5.88(s, 10H), 6.39(dd, 2H, J = 8.6&4.9Hz), 6.82–6.89 (m, 4H) |
| (a)-65 | 70.76 | 4.89 | 17.77 | δ 5.97(s, 10H), 6.72(dd, 2H, J = 6.8&1.6Hz), 7.35–7.46(m, 8H), 7.80(d, 2H, J = 8.0Hz), 8.53(d, 2H, J = 8.0Hz) |
| (a)-66 | 70.62 | 5.01 | 17.68 | δ 6.01(s, 10H), 7.10(dd, 2H, J = 8.8&2.3Hz), 7.21(d, 2H, J = 2.3 Hz), 7.23(ddd, 2H, J = 8.0, 6.8& 1.2Hz), 7.35(ddd, 2H, J = 8.0, 6.8& 1.2Hz), 7.70(d, 2H, J = 8.8Hz), 7.74(d, 2H, J = 8.0Hz), 7.75(d, 2H, J = 8.0Hz) |

TABLE 13-continued

| Catalyst component | Elementary analysis (wt %) | | | $^1$H-NMR spectral data (δ:ppm) |
|---|---|---|---|---|
| | C | H | Zr | |
| (a)-67 | 55.32 | 4.02 | 18.96 | δ 5.95(s, 10H), 6.59(dddd, 2H, J = 7.8, 7.2, 4.5&1.8Hz), 6.79–6.91(m, 4H), 6.95(t, 2H, J = 8.2Hz) |
| (a)-68 | 51.86 | 3.84 | 17.63 | δ 5.91(s, 10H), 6.52(td, 2H, J = 7.7, 7.7&1.7Hz), 6.58(td, 2H, J = 7.7, 7.7&1.4Hz)6.79(dd, 2H, J = 7.7&1.7Hz), 7.31(dd, 2H, J = J = 7.7&1.4Hz) |

EXAMPLE 69

Synthesis of Catalyst Component (b)-1 (Bis(methylcyclopentadienyl)bis(2-trifluoromethylphenoxy)zirconium)

The reaction was carried out under the same condition as in Example 1 except that 58.2 mg of $^2$-trifluoromethylphenol were added to 10 ml of toluene solution containing 53.9 mg of bis(methylcyclopentadienyl) dimethyl zirconium. After the completion of the reaction, toluene was distilled off under reduced pressure to yield a white solid (catalyst component (b)-1). The yield amount of the catalyst component (b)-1 was 109.7 mg corresponding to 99% yield.

The resulting product was confirmed as the final transition metal compound by means of $^1$H-NMR spectroscopy and the elementary analysis. The results were as follows:

$^1$H-NMR spectral data: δ 1.91 (s, 6H), 5.85 (t, 4H, J=2.3 Hz), 5.87(t, 4H, J=2.3 Hz), 6.59(t, 2H, J=7.8 Hz), 6.77(d, 2H, J=7.8 Hz), 7.09 (dt, 2H, J=7.8 and 1.5 Hz),7.48 (dd, 2H, J=7.8 and 1.5 Hz), elementary analysis: C 54.53, H 4.17, Zr 15.72

EXAMPLES 70 TO 74

Synthesis of Catalyst Components (b)-2 to (b)-6

The transition metal compounds were synthesized in the same manner as in Example 69 except that 2-trifluoromethylphenol to be reacted with bis(methylcyclopentadienyl)dimethyl zirconium was exchanged by the substituted phenol compounds as shown in Table 14 and the amount of each starting material was shown in Table 14 (Catalyst components are (b)-2 to (b)-6). The yield amount, yield and appearance of each catalyst component were summarized in Table 14 and the results of the elementary analysis and $^1$H-NMR spectral data in Table 15.

TABLE 14

| Example No. | Catalyst component | (MeCp)$_2$ZrMe$_2$ (used amount) (mg) | Substituted phenol compound | Usage (mg) | Yield amount (mg) | Yield (%) | Appearance |
|---|---|---|---|---|---|---|---|
| Ex. 69 | (b)-1 | 53.9 | 2-trifluoromethylphenol | 58.2 | 109.7 | 99 | white solid |
| Ex. 70 | (b)-2 | 55.0 | 3-trifluoromethylphenol | 58.7 | 113.7 | 100 | colorless oil |
| Ex. 71 | (b)-3 | 56.3 | 4-trifluoromethylphenol | 60.5 | 115.4 | 100 | colorless oil |
| Ex. 72 | (b)-4 | 58.7 | 2-tert-butylphenol | 62.9 | 117.4 | 100 | colorless oil |
| Ex. 73 | (b)-5 | 59.3 | 3-tert-butylphenol | 63.6 | 119.4 | 100 | colorless oil |
| Ex. 74 | (b)-6 | 71.2 | 4-tert-butylphenol | 76.5 | 144.5 | 100 | yellow oil |

TABLE 15

| Catalyst component | Elementary analysis (wt %) | | | $^1$H-NMR spectral data (δ:ppm) |
|---|---|---|---|---|
| | C | H | Zr | |
| (b)-1 | 54.53 | 4.17 | 15.72 | δ 1.91(s, 6H), 5.85(t, 4H, J = 2.3Hz), 5.87(t, 4H, J = 2.3Hz), 6.59(t, 2H, J = 7.8Hz), 6.77(d, 2H, J = 7.8Hz), 7.09(dt, 2H, J = 7.8, 7.8&1.5Hz), 7.48(dd, 2H, J = 7.8&1.5Hz) |
| (b)-2 | 54.48 | 4.07 | 15.79 | δ 1.94(s, 6H), 5.87(t, 4H, J = 2.8Hz), 5.91(t, 4H, J = 2.8Hz), 7.02(t, 2H, J = 7.8Hz), 7.05–7.09(m, 4H), 7.18 (s, 2H) |
| (b)-3 | 54.43 | 4.01 | 15.77 | δ 1.78(s, 6H), 5.64(t, 4H, J = 2.6Hz), 5.70(t, 4H, J = 2.6Hz), 6.52(d, 4H, J = 8.3Hz), 7.49(d, 4H, J = 8.3Hz) |
| (b)-4 | 70.16 | 7.69 | 16.44 | δ 1.54(s, 18H), 1.93(s, 6H), 5.95(t, 4H, J = 2.6Hz), 6.00(t, 4H, J = 2.6 Hz), 6.63(dd, 2H, J = 7.7&1.3Hz), 6.92(dt, 2H, J = 7.7, 7.7&1.3Hz), 7.15(dt, 2H, J = 7.7, 7.7&1.7Hz), 7.38(dd, 2H, J = 7.7&1.7Hz) |
| (b)-5 | 69.99 | 7.81 | 16.52 | δ 1.35(s, 18H), 2.00(s, 6H), 5.86(t, 4H, J = 2.5Hz), 5.90(t, 4H, J = 2.5 Hz), 6.70(ddd, 2H, J = 7.9, 2.1&1.0 Hz), 6.96(ddd, 2H, J = 7.9, 2.1&1.0 Hz), 7.05(t, 2H, J = 2.1Hz), 7.26(t, 2H, J = 7.9Hz) |
| (b)-6 | 70.02 | 7.35 | 16.62 | δ 1.33(s, 18H), 1.98(s, 6H), 5.84(t, 4H, J = 2.5Hz), 5.90(t, 4H, J = 2.5 Hz), 6.85(d, 4H, J = 8.7Hz), 7.33(d, 4H, J = 8.7Hz) |

EXAMPLE 75

Synthesis of Catalyst Component (c)-1 (Bis(n-butylcyclopentadienyl)bis(2-fluorophenoxy)zirconium)

The same reaction as well as treatment after the reaction was carried out as in Example 1 except that 69.8 mg of 2-fluorophenol was added to 10 ml of toluene solution containing 106.6 mg of bis(n-butylcyclopentadienyl)dimethyl zirconium and reacted. 162.9 mg of colorless oil product (catalyst component (c)-1) was obtained; yield: 100%. The resulting product was confirmed as the final transition metal compound by means of $^1$H-NMR spectroscopy and the elementary analysis. The results are as follows:

$^1$H-NMR spectral data: δ 0.77 (t, 6H, J=7.3 Hz), 1.13 (sext, 4H, J=7.5 Hz), 1.35 (quint, 4H, J=7.8 Hz), 2.43 (t, 4H, J=7.8 Hz), 5.94 (t, 4H, J=2.6 Hz), 5.97(t, 4H, J=2.6), 6.60 (dddd, 2H, J=7.8, 7.2, 4.5 and 1.8 Hz), 6.92 (tdd, 2H, J=7.8, 7.8, 1.5 and 0.5 Hz), 6.99 (dt, 2H, J=7.8, 7.8, and.1.8 Hz), 7.03 (ddd, 2H, J=11.4, 8.0, and 1.6 Hz), elementary analysis: C 64.76, H 6.18, Zr 16.39.

EXAMPLES 76 TO 83

Synthesis of Catalyst Components (c)-2 to (c)-9

The catalyst components were synthesized in the same manner as in Example 75 except that 2-fluorophenol to be reacted with bis(n-butylcyclopentadienyl)dimethyl zirconium was exchanged by the substituted phenol compounds as shown in Table 16 and 17 and the amount of each starting material was shown in Tables 16 and 17. The yield amount, yield and appearance of each catalyst component were summarized in Tables 16 and 17 and the results of $^1$H-NMR spectral data and the elementary analysis in Tables 18 and 19.

TABLE 18

| Catalyst component | Elementary analysis (wt %) | | | $^1$H-NMR spectral data (δ:ppm) |
|---|---|---|---|---|
| | C | H | Zr | |
| (c)-1 | 64.76 | 6.18 | 16.39 | δ 0.77(t, 6H, J = 7.3Hz), 1.13(sext, 4H, J = 7.5Hz), 1.35(quint, 4H, J = 7.8Hz), 2.43(t, 4H, J = 7.8Hz), 5.94(t, 4H, J = 2.6Hz), 5.97(t, 4H, J = 2.6Hz), 6.60(dddd, 2H, J = 7.8, 7.2, 4.5&1.8Hz), 6.92(tdd, 2H, J = 7.8, 7.8, 1.5&0.5Hz), 6.99(dt, 2H, J = 7.8, 7.8&1.8Hz), 7.03(ddd, 2H, J = 11.4, 8.0&1.6Hz) |
| (c)-2 | 64.71 | 6.34 | 15.99 | δ 0.77(t, 6H, J = 7.3Hz), 1.12(sext, 4H, J = 7.5Hz), 1.31(quint, 4H, J = 7.8Hz), 2.31(t, 4H, J = 7.8Hz), 5.80 (t, 8H, J = 1.6Hz), 6.52(ddd, 2H, J = 8.2, 2.1&0.8Hz), 6.55–6.61(m, 4H), 6.98(dt, 2H, J = 8.2, 8.2&7.4Hz) |
| (c)-3 | 64.41 | 6.44 | 16.84 | δ 0.79(t, 6H, J = 7.5Hz), 1.16(sext, 4H, J = 7.5Hz), 1.35(quint, 4H, J = 7.5Hz), 2.35(t, 4H, J = 7.5Hz), 5.85(s, 8H), 6.55(dd, 4H, J = 8.7&4.5Hz), 6.90(t, 4H, J = 8.7Hz) |

TABLE 19

| Catalyst component | Elementary analysis (wt %) | | | $^1$H-NMR spectral data (δ:ppm) |
|---|---|---|---|---|
| | C | H | Zr | |
| (c)-4 | 58.40 | 5.51 | 13.46 | δ 0.74(t, 6H, J = 7.3Hz), 1.10(sext, 4H, J = 7.5Hz), 1.30(quint, 4H, J = 7.6Hz), 2.44(t, 4H, J = 7.6Hz), 5.96 (t, 4H, J = 2.6Hz), 6.00(t, 4H, J = 2.6 Hz), 6.59(t, 2H, J = 7.6Hz), 6.83 |

TABLE 16

| Example No. | Catalyst component | (nBuCp)$_2$ZrMe$_2$ (used amount) (mg) | Substituted phenol compound | Usage (mg) | Yield amount (mg) | Yield (%) | Appearance |
|---|---|---|---|---|---|---|---|
| Ex. 75 | (c)-1 | 106.6 | 2-fluorophenol | 69.8 | 162.9 | 100 | colorless oil |
| Ex. 76 | (c)-2 | 97.5 | 3-fluorophenol | 69.1 | 150.4 | 100 | colorless oil |
| Ex. 77 | (c)-3 | 101.7 | 4-fluorophenol | 79.3 | 156.1 | 100 | colorless oil |
| Ex. 78 | (c)-4 | 76.5 | 2-trifluoromethylphenol | 67.3 | 138.2 | 99 | colorless oil |
| Ex. 79 | (c)-5 | 88.2 | 3-trifluoromethylphenol | 78.9 | 159.8 | 100 | colorless oil |
| Ex. 80 | (c)-6 | 80.3 | 4-trifluoromethylphenol | 71.7 | 146.4 | 100 | colorless oil |

TABLE 17

| Example No. | Catalyst component | (nBuCp)$_2$ZrMe$_2$ (used amount) (mg) | Substituted phenol compound | Usage (mg) | Yield amount (mg) | Yield (%) | Appearance |
|---|---|---|---|---|---|---|---|
| Ex. 81 | (c)-7 | 70.0 | 2-tert-butylphenol | 57.4 | 125.4 | 100 | colorless oil |
| Ex. 82 | (c)-8 | 74.7 | 3-tert-butylphenol | 61.6 | 133.3 | 100 | colorless oil |
| Ex. 83 | (c)-9 | 72.9 | 4-tert-butylphenol | 59.0 | 130.5 | 100 | colorless oil |

TABLE 19-continued

| Catalyst component | Elementary analysis (wt %) | | | $^1$H-NMR spectral data (δ:ppm) |
|---|---|---|---|---|
| | C | H | Zr | |
| | | | | (d, 2H, J = 8.1Hz), 7.12(ddd, 2H, J = 8.1, 7.6&1.5Hz), 7.49(dd, 2H, J = 7.6&1.5Hz) |
| (c)-5 | 58.84 | 5.36 | 13.74 | δ 0.77(t, 6H, J = 7.3Hz), 1.11(sext, 4H, J = 7.5Hz), 1.28(quint, 4H, J = 7.8Hz), 2.27(t, 4H, J = 7.8Hz), 5.75–5.79(m, 8H), 6.78(m, 2H, J = 7.7Hz), 7.01–7.08(m, 4H) |
| (c)-6 | 58.42 | 5.61 | 13.79 | δ 0.77(t, 6H, J = 7.3Hz), 1.11(sext, 4H, J = 7.5Hz), 1.27(quint, 4H, J = 7.7Hz), 2.26(t, 4H, J = 7.7Hz), 5.78 (t, 4H, J = 2.2Hz), 5.78(t, 4H, J = 2.2 Hz), 6.58(d, 4H, J = 8.5Hz), 7.50 (d, 4H, J = 8.5Hz) |
| (c)-7 | 72.40 | 8.15 | 14.30 | δ 0.74(t, 6H, J = 7.3Hz), 1.09(sext, 4H, J = 7.5Hz), 1.28(quint, 4H, J = 7.6Hz), 1.57(s, 18H), 2.47(t, 4H, J = 7.6Hz), 6.03(t, 4H, J = 2.6Hz), 6.13 (t,4H, J = 2.6Hz), 6.68(dd, 2H, J = 7.6&1.2Hz), 6.91(dt, 2H, J = 7.6, 7.6 &1.2Hz), 7.17(dt, 2H, J = 7.6, 7.6& 1.7Hz), 7.38(dd, 2H, J = 7.6&1.7Hz) |
| (c)-8 | 71.99 | 8.54 | 14.59 | δ 0.80(t, 6H, J = 7.3Hz), 1.18(sext, 4H, J = 7.5Hz), 1.36(s, 18H), 1.41 (quint, 4H, J = 7.8Hz), 2.48(t, 4H, J = 7.8Hz), 5.98(s, 8H), 6.37(ddd, 2H, J = 7.9, 2.1&0.8Hz), 6.96(ddd, 2H, J = 7.9, 2.1&0.8Hz), 7.05(t, 2H, J = 2.1Hz), 7.27(t, 2H, J = 7.9Hz) |
| (c)-9 | 72.17 | 8.44 | 14.38 | δ 0.79(t, 6H, J = 7.3Hz), 1.17(sext, 4H, J = 7.5Hz), 1.32(s, 18H), 1.38 (quint, 4H, J = 7.8Hz), 2.47(t, 4H, J = 7.8Hz), 5.96(s, 8H), 6.88(d, 4H, J = 8.6Hz), 7.34(d, 4H, J = 8.6Hz) |

EXAMPLE 84

Synthesis of Catalyst Component (d)-1(Bis(1,3-dimethylcyclopentadienyl)bis(2-trifluoromethylphenoxy)zirconium The reaction was carried out under the same condition as in Example 1 except that 62.5 mg of 2-trifluoromethylphenol were added to 10 ml of toluene solution containing 59.3 mg of bis(1,3-dimethylcyclopentadienyl)dimethyl zirconium. The product was recrystallized from toluene to yield the transition metal compound as white crystal (catalyst component (d)-1). The yield amount was 63.1 mg corresponding to 53% yield.

The resulting product was confirmed as the final transition metal compound by means of $^1$H-NMR spectroscopy and the elementary analysis. The results are shown as follows:

$^1$H-NMR spectral data: δ 1.95 (s, 12H), 5.72 (t, 2H, J=2.4 Hz), 5.77 (d, 4H, J=2.4 Hz), 6.58 (t, 2H, J=7.8 Hz), 6.78(d, 2H, J=7.8 Hz), 7.06 (t, 2H, J=7.8 Hz), 7.49 (dd, 2H, J=7.8, and 1.6 Hz), elementary analysis : C 55.82, H 4.63, Zr 15.09.

EXAMPLES 85 TO 89

Synthesis of Catalyst Components (d)-2 to (d)-6

The reaction was carried out in the same manner as in Example 84 except that 2-trifluoromethylphenol to be reacted with bis(1,3-dimethylcyclopentadienyl)dimethyl zirconium was exchanged by the substituted phenol compounds as shown in Table 20 and the amount of each starting material was shown in Table 20. The yield amount, yield and appearance of each catalyst component were summarized in Table 20 and the results of elementary analysis and $^1$H-NMR spectral data in Table 21.

TABLE 20

| Example No. | Catalyst component | (MeCp)$_2$ZrMe$_2$ (used amount) (mg) | Substituted phenol compound | Usage (mg) | Yield amount (mg) | Yield (%) | Appearance |
|---|---|---|---|---|---|---|---|
| Ex. 84 | (d)-1 | 59.3 | 2-trifluoromethylphenol | 62.5 | 63.1 | 53 | white crystal |
| Ex. 85 | (d)-2 | 55.9 | 3-trifluoromethylphenol | 58.9 | 110.7 | 100 | yellow oil |
| Ex. 86 | (d)-3 | 59.9 | 4-trifluoromethylphenol | 63.3 | 115.8 | 99 | colorless oil |
| Ex. 87 | (d)-4 | 53.6 | 2-tert-butylphenol | 52.4 | 102.5 | 100 | white solid |
| Ex. 88 | (d)-5 | 51.1 | 3-tert-butylphenol | 50.4 | 96.9 | 100 | colorless oil |
| Ex. 89 | (d)-6 | 59.5 | 4-tert-butylphenol | 58.1 | 114.9 | 100 | white solid |

TABLE 21

| Catalyst component | Elementary analysis (wt %) | | | $^1$H-NMR spectral data (δ:ppm) |
|---|---|---|---|---|
| | C | H | Zr | |
| (d)-1 | 55.82 | 4.63 | 15.09 | δ 1.95(s, 12H), 5.72(t, 2H, J = 2.4Hz), 5.77(d, 4H, J = 2.4Hz), 6.58 (t, 2H, J = 7.8Hz), 6.78(d, 2H, J = 7.8Hz), 7.06(t, 2H, J = 7.8Hz), 7.49 (dd, 2H, J = 7.8&1.6Hz) |
| (d)-2 | 55.97 | 4.56 | 15.13 | δ 1.78(s, 12H), 5.51(d, 4H, J = |

TABLE 21-continued

| Catalyst component | Elementary analysis (wt %) | | | ¹H-NMR spectral data (δ:ppm) |
|---|---|---|---|---|
| | C | H | Zr | |
| (d)-3 | 56.17 | 4.27 | 15.25 | 2.4Hz), 5.57(t, 2H, J = 2.4Hz), 6.77 (d, 2H, J = 7.8Hz), 7.00(t, 2H, J = 7.8Hz), 7.05(t, 2H, J = 7.8Hz) δ 1.78(s, 12H), 5.53(d, 2H, J = 2.5Hz), 5.58(t, 4H, J = 2.5Hz), 6.56 (d, 4H, J = 8.4Hz), 7.45(d, 4H, J = 8.4Hz) |
| (d)-4 | 71.01 | 7.78 | 15.86 | δ 1.54(s, 18H), 1.96(s, 12H), 5.86(d, 4H, J = 2.4Hz), 6.03(t, 2H, J = 2.4 |

TABLE 21-continued

| Catalyst component | Elementary analysis (wt %) | | | ¹H-NMR spectral data (δ:ppm) |
|---|---|---|---|---|
| | C | H | Zr | |
| (d)-5 | 70.72 | 8.04 | 15.67 | Hz), 6.71(dd, 2H, J = 7.7&1.2Hz), 6.93(dt, 2H, J = 7.7, 7.7&1.2Hz), 7.19(dt, 2H, J = 7.7, 7.7&1.8Hz), 7.38(dt, 2H, J = 7.7, 7.7&1.8Hz) δ 1.32(s, 18H), 2.00(s, 12H), 5.70(d, 4H, J = 2.4Hz), 5.84(t, 2H, J = 2.4 Hz), 6.74(ddd, 2H, J = 7.8, 2.1& 0.8Hz), 6.93(ddd, 2H, J = 7.8, 2.1& 0.8Hz), 7.02(t, 2H, J = 2.1Hz), 7.23 (t, 2H, J = 7.8Hz) |
| (d)-6 | 70.75 | 7.82 | 15.43 | δ 1.31(s, 18H), 1.98(s, 12H), 5.68(d, 4H, J = 2.4Hz), 5.82(t, 2H, J = 2.4 Hz), 6.86(d, 4H, J = 8.6Hz), 7.29(d, 4H, J = 8.6Hz) |

EXAMPLE 90

Synthesis of Catalyst Component (e)-1 (Bis(pentamethylcyclopentadienyl)bis(2-fluorophenoxy) zirconium)

The reaction was carried out in the same condition as in Example 1 except that 123.3 mg of 2-fluorophenol were added to 10 ml of toluene solution containing 237.7 mg of bis(pentamethylcyclopentadienyl)dimethyl zirconium and reacted. The product was recrystallized from toluene to yield the transition metal compound as white crystal (catalyst component (e)-1). The yield amount was 210.7 mg corresponding to 66% yield.

The result of ¹H-NMR spectroscopy and the elementary analysis of product are summarized as follows:

¹H-NMR spectral data: δ 1.85 (s, 30H), 6.59 (dddd, 2H, J =7.5, 7.2, 4.4 and 1.6 Hz), 6.96(dddd, 2H, J=8.4, 7.2, 1.6 and 0.7 Hz), 7.03 (ddd, 2H, J=11.8, 7.5 and 1.6 Hz), 7.19(d, 2H, J=8.4 Hz), elementary analysis: C 65.71, H 6.77, Zr 15.71

EXAMPLE 91 TO 92

Synthesis of Catalyst Components (e)-2 and (e)-3

The catalyst components were synthesized in the same manner as in Example 90 except that 2-fluorophenol to be reacted with bis(pentamethylcyclopentadienyl)dimethyl zirconium was exchanged by the substituted phenol compounds as shown in Table 22 and the amount of each starting material was shown in Table 22. The yield amount, yield and appearance of each catalyst component were summarized in Table 22 and the results of elementary analysis and ¹H-NMR spectroscopy in Table 23.

TABLE 22

| Example No. | Catalyst component | (MeCp)₂ZrMe₂ (used amount) (mg) | Substituted phenol compound | Usage (mg) | Yield amount (mg) | Yield (%) | Appearance |
|---|---|---|---|---|---|---|---|
| Ex. 90 | (e)-1 | 237.7 | 2-fluorophenol | 123.3 | 210.7 | 66 | white crystal |
| Ex. 91 | (e)-2 | 220.2 | 3-fluorophenol | 114.1 | 52.6 | 18 | white crystal |
| Ex. 92 | (e)-3 | 245.7 | 4-fluorophenol | 127.3 | 183.6 | 55 | white crystal |

TABLE 23

| Catalyst component | Elementary analysis (wt %) | | | ¹H-NMR spectral data (δ:ppm) |
|---|---|---|---|---|
| | C | H | Zr | |
| (e)-1 | 65.71 | 6.77 | 15.71 | δ 1.85(s, 30H), 6.59(dddd, 2H, J = 7.5, 7.2, 4.4&1.6Hz), 6.96(dddd, 2H, J = 8.4, 7.2, 1.6&0.7Hz), 7.03 (ddd, 2H, J = 11.8, 7.5&1.6Hz), 7.19(d, 2H, J = 8.4Hz) |
| (e)-2 | 65.49 | 6.72 | 15.46 | δ 1.74(s, 30H), 6.54(tdd, 2H, J = 8.2, 8.2, 2.3&0.8Hz), 6.64(ddd, 2H, J = 8.2, 2.3&0.8Hz), 6.99(dt, 2H, J = 11.5, 2.3&2.3Hz), 6.99(td, 2H, J = 8.2, 8.2&7.5Hz) |
| (e)-3 | 65.42 | 7.04 | 15.22 | δ 1.79(s, 30H), 6.64(dd, 4H, J = 9.0 &4.5Hz), 6.89(dd, 4H, J = 9.0& 8.4Hz) |

EXAMPLE 93

Synthesis of Catalyst Component (f)-1 (Ethylenebis(indenyl)bis(2-trifluoromethylphenoxy)zirconium)

The same reaction as well as treatment after the reaction was carried out as in Example 1 except that 60.4 mg of 2-trifluoromethylphenol were added to 10 ml of toluene solution containing 70.3 mg of ethylenebis(indenyl) dimethyl zirconium. 124.5 mg of colorless oily product were obtained in a yield of 100%.

The results of ¹H-NMR spectroscopy and the elementary analysis of the product are shown as follows:

¹H-NMR spectral data: δ 2.60–2.85 (m, 4H), 5.63 (d, 2H, J=3.2 Hz), 6.40 (d, 2H, J=3.2 Hz), 6.57 (t, 2H, J=7.8 Hz), 6.79 (d, 2H, J=7.8 Hz), 6.90 (dd, 4H, J=6.5 and 3.3 Hz), 7.09 (dt, 2H, J=7.8, 7.8 and 1.6 Hz), 7.24 (dd, 4H, J=6.5, and 3.3 Hz), 7.52 (dd, 2H, J=7.8 and 1.6 Hz), elementary analysis: C 60.82, H 3.92, Zr 13.41.

EXAMPLES 94 TO 95

Synthesis of Catalyst Components (f)-2 and (f)-3

The catalyst components were synthesized in the same manner as in Example 93 except that 2-trifluoromethylphenol to be reacted with ethylenebis(indenyl)dimethyl zirconium was exchanged by the substituted phenol compounds as shown in Table 24 and the amount of each starting material was shown in Table 24. The yield amount, yield and appearance of each catalyst component are summarized in Table 24 and the results of elementary analysis and $^1$H-NMR spectroscopy in Table 25.

TABLE 24

| Example No. | Catalyst component | Et(Ind)$_2$ZrMe$_2$ (used amount) (mg) | Substituted phenol compound | Usage (mg) | Yield amount (mg) | Yield (%) | Appearance |
|---|---|---|---|---|---|---|---|
| Ex. 93 | (f)-1 | 70.3 | 2-trifluoromethylphenol | 60.4 | 124.5 | 100 | colorless oil |
| Ex. 94 | (f)-2 | 65.9 | 3-trifluoromethylphenol | 56.6 | 42.5 | 36 | white crystal |
| Ex. 95 | (f)-3 | 72.5 | 4-trifluoromethylphenol | 62.2 | 126.8 | 99 | white solid |

TABLE 25

| Catalyst component | Elementary analysis (wt %) | | | $^1$H-NMR spectral data (δ:ppm) |
|---|---|---|---|---|
| | C | H | Zr | |
| (f)-1 | 60.82 | 3.92 | 13.41 | δ 2.60–2.85(m, 4H), 5.63(d, 2H, J = 3.2Hz), 6.40(d, 2H, J = 3.2Hz), 6.57 (t, 2H, J = 7.8Hz), 6.79(d, 2H, J = 7.8Hz), 6.90(dd, 4H, J = 6.5&3.3 Hz), 7.09(dt, 2H, J = 7.8, 7.8&1.6 Hz), 7.24(dd, 4H, J = 6.5&3.3Hz), 7.52(dd, 2H, J = 7.8&1.6Hz) |
| (f)-2 | 60.90 | 3.76 | 13.47 | δ 2.58–2.86(m, 4H), 5.67(d, 2H, J = 3.4Hz), 6.41(d, 2H, J = 3.4Hz), 6.80 (d, 2H, J = 7.7Hz), 6.91(dd, 4H, J = 6.5&3.3Hz), 7.01(t, 2H, J = 7.7Hz), 7.06(t, 2H, J = 7.7Hz), 7.14(s, 2H), 7.21(dd, 4H, J = 6.5&3.3Hz) |
| (f)-3 | 60.73 | 3.86 | 13.39 | δ 2.61–2.79(m, 4H), 5.65(d, 2H, J = 3.3Hz), 6.41(d, 2H, J = 3.3Hz), 6.59 (d, 4H, J = 8.5Hz), 6.91(dd, 4H, J = 6.4&3.4Hz), 7.22(dd, 4H, J = 6.4& 3.4Hz), 7.43(d, 4H, J = 8.5Hz) |

II. Polymerization and Copolymerization

EXAMPLE 96

To a 800 ml autoclave having been dried sufficiently and exchanged by ethylene, 5 ml of toluene solution containing 0.05 μmol of catalyst component (a)-1 and 0.9 ml of toluene solution of methylaluminoxane (aluminum content 1.5 mmol) manufactured by Tosoaczo Co. (Trade name: MMAO) were introduced with 300 ml of toluene. The inner temperature of the autoclave was raised at 70° C., and ethylene gas was introduced up to 0.3 MPa. Polymerization was carried out for 1 hr while keeping the pressure. After discharging ethylene, a small amount of isopropyl alcohol was added to terminate the polymerization. The resulting polymer was isolated and dried to yield 12.1 g of polymer. The activity per unit zirconium was 2640 kg polymer/g Zr.

COMPARATIVE EXAMPLE 1

(1)Synthesis of Catalyst Component (r)-1 (Dicyclopentadienyldiphenoxy zirconium)

The reaction of dicyclopentadienyldimethyl zirconium and phenol was carried out in the same manner as in Example 1 except that phenol was used instead of orthocresol. A product of white solid was obtained (catalyst component (r)-1). The product was confirmed as the dicyclopentadienyldiphenoxy zirconium by means of $^1$H-NMR spectroscopy.

(2) Polymerization:

The polymerization of ethylene was carried out in the same manner as in Example 96 except that 5 ml of toluene solution containing 0.05 μmol of the product obtained in the above (1) instead of catalyst component (a)-1 was used. As a result, 5.2 g of polymer were obtained and the activity per unit zirconium was 1140 kg polymer/g Zr. It is clear that the activity of this is lower than that of the transition metal compound of Example 1 having the same cyclopentadienyl ligand portion.

COMPARATIVE EXAMPLE 2

(1) Synthesis of Catalyst Component (r)-2 (Dicyclopentadienyldithiophenoxy zirconium)

The reaction of dicyclopentadienyldimethyl zirconium and thiophenol was carried out in the same manner as in Example 1 that thiophenol was used instead of orthocresol. A product of pale yellow solid was obtained.

(2) Polymerization

The polymerization of ethylene was carried out in the same manner as in Example 96 except that 5 ml of toluene solution containing 0.05 μmol of the product obtained in the above (1) instead of catalyst component (a)-1 was used. As a result, 4.0 g of polymer was obtained and the activity per unit zirconium was 880 kg polymer/g Zr. It is clear that the activity of this catalyst component (r)-2 is lower than that of the transition metal compound of Example 67 having the same cyclopentadienyl ligand portion.

EXAMPLES 97–135

The polymerization of ethylene was carried out in the same manner as in Example 96 except that the catalyst components produced in Examples 2–68 respectively were used instead of the catalyst component (a)-1. The results are summarized in Tables 26 to 28.

TABLE 26

| Example No. | Catalyst component | Catalyst Usage (μmol) | polymer yield (g) | activity (kg polymer/ g Zr) |
|---|---|---|---|---|
| Comparative Example 1 | (r)-1 | 0.05 | 5.2 | 1140 |
| Example 96 | (a)-1 | 0.05 | 12.1 | 2640 |
| Example 97 | (a)-3 | 0.05 | 7.6 | 1650 |
| Example 98 | (a)-6 | 0.05 | 8.0 | 1740 |
| Example 99 | (a)-7 | 0.05 | 13.5 | 2950 |
| Example 100 | (a)-9 | 0.05 | 9.3 | 2050 |
| Example 101 | (a)-11 | 0.05 | 13.6 | 2990 |

TABLE 26-continued

| Example No. | Catalyst component | Catalyst Usage (µmol) | polymer yield (g) | activity (kg polymer/ g Zr) |
|---|---|---|---|---|
| Example 102 | (a)-12 | 0.05 | 9.2 | 2020 |
| Example 103 | (a)-15 | 0.05 | 7.6 | 1660 |
| Example 104 | (a)-16 | 0.05 | 12.0 | 2630 |
| Example 105 | (a)-17 | 0.05 | 10.5 | 2310 |
| Example 106 | (a)-19 | 0.05 | 9.0 | 1970 |
| Example 107 | (a)-23 | 0.05 | 10.1 | 2210 |
| Example 108 | (a)-24 | 0.05 | 10.6 | 2330 |
| Example 109 | (a)-25 | 0.05 | 11.4 | 2500 |
| Example 110 | (a)-26 | 0.05 | 10.1 | 2210 |
| Example 111 | (a)-27 | 0.05 | 10.2 | 2230 |

TABLE 27

| Example No. | Catalyst component | Catalyst Usage (µmol) | polymer yield (g) | activity (kg polymer/ g Zr) |
|---|---|---|---|---|
| Example 112 | (a)-28 | 0.05 | 13.1 | 2860 |
| Example 113 | (a)-30 | 0.05 | 11.7 | 2570 |
| Example 114 | (a)-32 | 0.05 | 8.4 | 1840 |
| Example 115 | (a)-34 | 0.05 | 13.1 | 2890 |
| Example 116 | (a)-35 | 0.05 | 9.1 | 1980 |
| Example 117 | (a)-3W | 0.05 | 11.1 | 2440 |
| Example 118 | (a)-39 | 0.05 | 9.7 | 2120 |
| Example 119 | (a)-42 | 0.05 | 8.8 | 1930 |
| Example 120 | (a)-43 | 0.05 | 9.6 | 2100 |
| Example 121 | (a)-46 | 0.05 | 8.7 | 1900 |
| Example 122 | (a)-47 | 0.05 | 8.0 | 1750 |
| Example 123 | (a)-48 | 0.05 | 7.8 | 1720 |
| Example 124 | (a)-49 | 0.05 | 10.9 | 2380 |
| Example 125 | (a)-54 | 0.05 | 7.7 | 1690 |
| Example 126 | (a)-57 | 0.05 | 8.1 | 1780 |
| Example 127 | (a)-58 | 0.05 | 10.9 | 2380 |
| Example 128 | (a)-59 | 0.05 | 14.2 | 3110 |

TABLE 28

| Example No. | Catalyst component | Catalyst Usage (µmol) | polymer yield (g) | activity (kg polymer/ g Zr) |
|---|---|---|---|---|
| Eample 129 | (a)-60 | 0.05 | 11.3 | 2480 |
| Example 130 | (a)-61 | 0.05 | 12.1 | 2640 |
| Example 131 | (a)-62 | 0.05 | 11.4 | 2500 |
| Example 132 | (a)-64 | 0.05 | 15.8 | 3460 |
| Example 133 | (a)-65 | 0.05 | 9.6 | 2110 |
| Comparative Example 2 | (r)-2 | 0.05 | 4.0 | 880 |
| Example 134 | (a)-67 | 0.05 | 6.7 | 1470 |
| Example 135 | (a)-68 | 0.05 | 7.8 | 1700 |

EXAMPLES 136–162

The polymerization of ethylene was carried out in the same manner as in Example 96 except that instead of catalyst component (a)-1 the catalyst components ((b)-1 to (b)-6, (c)-1 to (c)-9 and (d)-1 to (d)-6) and the amount of catalyst component as shown in Tables 29 and 30 were used. The results are summarized in Tables 29 and 30.

COMPARISON EXAMPLE 3

(1) Synthesis of Catalyst Component (r)-3 (Bis (methylcyclopentadienyl)diphenoxy zirconium)

The reaction of bis(methylcyclopentadienyl)dimethyl zirconium and phenol was carried out in the same manner as in Example 69 except that phenol was used instead of 2-trifluoromethylphenol; A product of white crystal was obtained.

(2) Polymerization

The polymerization of ethylene was carried out in the same manner as in Example 96 except that 5 ml of toluene solution containing $0.05$ µmol of the product obtained in the above (1) was used instead of the catalyst component (a)-1. The results are shown in Table 29. The activity of the catalyst component (r)-3 is lower than that of the transition metal compounds having the same cyclopentadienyl ligand portion, as shown, respectively in examples.

COMPARATIVE EXAMPLE 4

(1) Synthesis of Catalyst Component (r)-4 (Bis(n-butylcyclopentadienyl)diphenoxy Zirconium)

The reaction of bis(n-butylcyclopentadienyl)dimethyl zirconium and phenol was carried out in the same manner as in Example 75 except that phenol was used instead of 2-fluorophenol; A colorless oil product was obtained.

(2) Polymerization

The polymerization of ethylene was carried out in the same manner as in Example 96 except that 5 ml of toluene solution containing 0.03 µmol of the product obtained in the above (1) was used instead of the catalyst component (a)-1; The results as shown in Table 30 were obtained. The activity of the catalyst component (r)-4 is lower than that of the transition metal compounds having the same cyclopentadienyl ligand portion as shown, respectively, in examples.

COMPARATIVE EXAMPLE 5

(1) Synthesis of Catalyst Component (r)-5 (Bis(1,3-dimethylcyclopentadienyl)diphenoxy zirconium)

The reaction of bis (1,3-dimethylcyclopentadienyl) dimethyl zirconium and phenol was carried out in the same manner as in Example 84 except that phenol was used instead of 2-trifluoromethylphenol; A product of white solid was obtained.

(2) Polymerization

The polymerization of ethylene was carried out in the same manner as in Example 96 except that 5 ml of toluene solution containing 0.03 µmol of the product obtained in the above (1) instead of catalyst component (a)-1 was used; The results as shown in Table 30 were obtained. The activity of the catalyst component (r)-5 is lower than that of the transition metal compounds having the same cyclopentadienyl ligand portion, as shown, respectively in examples.

TABLE 29

| Example No. | Catalyst component | Catalyst Usage (µmol) | polymer yield (g) | activity (kg polymer/ g Zr) |
|---|---|---|---|---|
| Example 136 | (b)-1 | 0.05 | 8.7 | 1910 |
| Example 137 | (b)-2 | 0.05 | 9.7 | 2120 |
| Example 138 | (b)-3 | 0.05 | 7.8 | 1700 |
| Example 139 | (b)-4 | 0.05 | 14.9 | 3270 |
| Example 140 | (b)-5 | 0.05 | 16.4 | 3600 |
| Example 141 | (b)-6 | 0.05 | 11.1 | 2440 |
| Comparative Example 3 | (r)-3 | 0.05 | 5.0 | 1110 |

TABLE 30

| Example No. | Catalyst component | Catalyst Usage (μmol) | polymer yield (g) | activity (kg polymer/ g Zr) |
|---|---|---|---|---|
| Example 142 | (c)-1 | 0.03 | 15.8 | 5760 |
| Example 143 | (c)-2 | 0.03 | 18.0 | 6560 |
| Example 144 | (c)-3 | 0.03 | 16.1 | 5870 |
| Example 145 | (c)-4 | 0.03 | 19.7 | 7190 |
| Example 146 | (c)-5 | 0.03 | 19.2 | 7020 |
| Example 147 | (c)-6 | 0.03 | 14.5 | 5300 |
| Example 148 | (c)-7 | 0.03 | 8.8 | 3220 |
| Example 149 | (c)-8 | 0.03 | 17.1 | 6240 |
| Example 150 | (c)-9 | 0.03 | 14.9 | 5450 |
| Comparative Example 4 | (r)-4 | 0.03 | 10.1 | 3680 |
| Example 151 | (d)-1 | 0.03 | 8.6 | 3140 |
| Example 152 | (d)-2 | 0.03 | 7.1 | 2580 |
| Example 153 | (d)-3 | 0.03 | 8.0 | 2940 |
| Example 154 | (d)-4 | 0.03 | 9.4 | 3440 |
| Example 155 | (d)-5 | 0.03 | 8.3 | 3020 |
| Example 156 | (d)-6 | 0.03 | 8.0 | 2920 |
| Comparative Example 5 | (r)-5 | 0.03 | 5.4 | 1980 |

EXAMPLE 157

Copolymerization of Ethylene and 1-Hexene

Ethylene was polymerized while being introduced continuously in the same manner as in Example 96 except that 300 ml of toluene and 10 ml of 1-hexene were fed to an autoclave and 5 ml of toluene solution containing 0.1 μmol of the catalyst component (a)-19 was used. After discharging ethylene, a small amount of isopropyl alcohol was added to terminate the polymerization. The resulting polymer was isolated and dried to yield 13.9 g of polymer. The activity per unit zirconium was 1,520 kg polymer/g Zr. It was confirmed that the polymer was the copolymer of ethylene and 1-hexene by means of $^{13}$C-NMR spectroscopy. The comonomer content in the polymer was 1.13 mol%.

EXAMPLE 158

Copolymerization of Ethylene and 1-Hexene 300 ml of toluene and 6.7 ml of 1-hexene were fed to an autoclave, 0.25 mmol of triisobutyl aluminum, 0.1 μmol of the catalyst component (a)-7 and 2.0 μmol of triphenylmethyltetrakis(pentafluorophenyl)borate were added in order, the mixture was heated to 70° C. and polymerization was carried out for 1 hr while feeding ethylene continuously in such a manner that the partial pressure of ethylene was 0.3 MPa. The polymer was isolated and dried to yield 13.1 g of polymer. The activity per unit zirconium was 1,430 kg polymer/g Zr. The content of 1-hexene in the polymer was determined as 1.33 mol %.

EXAMPLE 159

Copolymerization of Ethylene and 1, 9-Decadiene

The polymerization was carried out while feeding ethylene in the same manner as in Example 96 except that 300 ml of toluene and 11.0 g of 1, 9-decadiene were fed to an autoclave and 0.1 μmol of the catalyst component (a)-7 was added. The resulting polymer was subjected to the post-treatment to yield 11.6 g of polymer. The activity per unit zirconium was 1,260 kg polymer/g Zr. It was confirmed that the polymer was the copolymer of ethylene and 1, 9-decadiene from $^1$H-NMR spectral data, and the comonomer content in the polymer was 1.02 mol %.

EXAMPLE 160

Copolymer of Ethylene and 2-Norbornene 90 ml of toluene and 10 ml (30 mmol) of 2-norbornene were added to an autoclave and then 3.7 ml of toluene solution of methylalminoxane (corresponding to 6.0 mmol of aluminum) and 1 ml of toluene solution containing 1 μmol of the catalyst component (d)-3 were added. The inner temperature of autoclave was kept at 60° C., ethylene gas was introduced up to 0.3 MPa and the mixture was polymerized for 30 min while keeping the pressure. The resulting polymer solution was diluted with toluene, then treated with aq.0.6N-HCl solution and water, then, added with a large amount of methanol to separate the polymer. After filtrating and drying the polymer, 3.13 g of polymer was obtained and the activity per unit zirconium was 34.3 kg polymer/g Zr. It was confirmed that the polymer was the copolymer of ethylene and 2-norbornene from $^{13}$H-NMR spectral data. The content of 2-norbornene in the polymer was 13.4 mol %.

EXAMPLE 161–163

The copolymerization of ethylene and 2-norbornene was carried out in the same manner as in Example 160 except that catalyst components (f)-1–(f)-3 were used instead of the catalyst component (d)-3. The results are summarized in Table 31.

COMPARATIVE EXAMPLE 6

(1) Synthesis of Catalyst Component (r)-6 (Ethylenebis(indenyl)diphenoxy zirconium)

The reaction of ethylenebis(indenyl) dimethyl zirconium and phenol was carried out in the same manner as in Example 93 except that phenol was used instead of 2-trifluoromethylphenol. A catalyst component of colorless oil was obtained.

(2) Polymerization

The copolymerization of ethylene and 2-norbornene was carried out in the same manner as in Example 160 except that 5 ml of toluene solution containing 1.0 μmol of the catalyst component (r)-6 was used instead of the catalyst component (d)-3. The results are shown in Table 31.

TABLE 31

| Example No. | Catalyst component | polymer yield (g) | activity (kg polymer/ gZr) | contents of 2-norbornene (mol %) |
|---|---|---|---|---|
| Example 161 | (f)-1 | 1.50 | 16.5 | 16.9 |
| Example 162 | (f)-2 | 2.27 | 24.9 | 18.6 |
| Example 163 | (f)-3 | 2.47 | 27.1 | 20.7 |
| Comparative Example 6 | (r)-6 | 0.81 | 8.9 | 11.4 |

EXAMPLE 164

Copolymerization of Ethylene and Dicyclopentadiene

The polymerization was carried out under the same condition as in Example 160 except that 90 ml of toluene and 4.1 ml of dicyclopentadiene (30 mmol) were added to an autoclave. The yield amount of polymer was 3.01 g and the activity per unit zirconium was 33.0 kg polymer/g Zr. The content of dicyclopentadiene in the polymer was 24.1 mol %.

III. Durability Test of Catalyst

EXAMPLE 165

(1) Preparation of Catalyst Component Solution

The procedure for the preparation of catalyst component solution was carried out in an air atmosphere. 70 mg of the catalyst component (a)-7 was put into a 50 ml conical flask and dissolved in 50 ml of toluene. Then, 5 ml of the solution of the catalyst component was taken out and diluted with toluene up to 25 ml of total volume to obtain 0.5 μmol/l of catalyst concentration.

(2) Polymerization Test

The polymerization of ethylene was carried out in the same manner as in Example 96 by using the solution of catalyst component just after the preparation thereof and after stirring with a magnetic stirrer for 24 hours, respectively. The results of polymerization are shown in Table 32.

COMPARATIVE EXAMPLE 7

The solution containing 0.5 μmol/l of dicyclopentadienyl dimethyl zirconium instead of the catalyst component (a)-7 was prepared in the same manner as in Example 165 and the polymerization was carried out with the solution in the same manner as in Example 165. The results are shown in Table 32. The degree of reduction of activity was very large when the solution of catalyst component stirred for 24 hours was used in the case of comparative are shown in Table 32. The degree of reduction of activity was very large when the solution of catalyst component stirred for 24 hours was used in the case of comparative example 7, whereas the degree of the reduction was very small when the solution of catalyst component stirred for 24 hours was used in the case of example 165.

TABLE 32

| Example No. | Treatment of the solution of catalyst component | Catalyst Usage (μmol) | polymer yield (g) | activity (kg polymer/ g Zr) |
|---|---|---|---|---|
| Example 165 | immediately after dilution | 0.05 | 13.9 | 3030 |
|  | after stirring for 24 hours | 0.05 | 13.3 | 2900 |
| Comparative Example 7 | immediately after dilution | 0.05 | 11.3 | 2460 |
|  | after stirring for 24 hours | 0.05 | 6.5 | 1420 |

According to the present invention, the transition metal compound as catalyst component for the polymerization of olefins, does not contain a halogen bound directly to the metal so that hydrogen halide causing corrosion is not generated by hydrolysis, of the transition metal compound, and has a high stability to oxygen and moisture so that it may be easily handled and stored in good stability. Further, the catalyst containing the transition, metal compound according to the present invention shows an excellent activity for the homo- and copolymerization of olefins.

What is claimed is:

1. A catalyst for the polymerization of olefins comprising:

[A] a catalyst component comprising a transition metal compound represented by the general formula [1] or [2]:

$$(R_a Cp)_m(R'_b Cp)_n M(-X-Ar-Y_c)_{4-(m+n)} \quad [1]$$

wherein M represents titanium, zirconium or hafnium, Cp represents a radical having the cyclopentadienyl skeleton, R and R' each represents a hydrogen atom, an alkyl, an alkenyl, an aryl, an alkylaryl, an arylalkyl or an alkylsilyl radical, X represents an oxygen or a sulphur atom, Ar represents an aromatic ring, Y represents a hydrogen atom, a hydrocarbon radical, a silyl radical, a halogen atom, a halogenated hydrocarbon radical, a nitrogen-containing organic radical, an oxygen-containing organic radical or a sulphur-containing organic radical, each of a and b is an integer of 0 to 5, each of m and n is an integer of 0 to 3 and m+n is an integer of 1 to 3, and c is an integer of 1 to 5, with a proviso that Y is not a hydrogen atom when Ar is a benzene ring;

$$R''(R_d Cp) (R'_e Cp)M(-X-Ar-Y_c)_2 \quad [2]$$

wherein M represents titanium, zirconium or hafnium, Cp represents a radical having the cyclopentadienyl skeleton, R and R' each represents a hydrogen atom, an alkyl, an alkenyl, an aryl, an alkylaryl, an arylalkyl or an alkylsilyl radical, R" represents a divalent radical which links $(R_d Cp)$ and $(R'_e Cp)$ and is selected from the group consisting of an alkylene, an arylalkylene, a dialkylsilylene, a dialkylgermylene, an alkylphosphindiyl or an alkylimino radical, X represents an oxygen or a sulphur atom, Ar represents an aromatic ring, Y represents a hydrogen atom, a hydrocarbon radical, a silyl radical, a halogen atom, a halogenated hydrocarbon radical, a nitrogen-containing organic radical, an oxygen-containing organic radical or a sulphur-containing organic radical, each of d and e is an integer of 0 to 4, and c is an integer of 1 to 5, with a proviso that Y is not a hydrogen atom when Ar is a benzene ring; and

[B] an organic aluminum oxy compound or a cation generator.

2. A catalyst for the polymerization of olefins according to the claim 1, wherein Ar represents a benzene or naphthalene ring in the general formula [1] and [2].

3. A catalyst for the polymerization of olefins according to claim 1, wherein Y is a substituent selected from the group consisting of a hydrogen atom, an alkyl radical having 1 to 10 carbon atoms, an aryl radical having 6 to 10 carbon atoms, an alkenyl radical having 2 to 10 carbon atoms, an alkynyl radical having 2 to 10 carbon atoms, an arylalkyl radical having 7 to 20 carbon atoms, an arylalkenyl radical having 8 to 20 carbon atoms, an alkylaryl radical having 7 to 20 carbon atoms; a silyl radical; a halogen atom, a halogenated hydrocarbon radical; cyano, nitro, nitroso, isocyanide, cyanate, isocyanate, amino, amido; alkoxy, aryloxy, acyl, alkoxycarbonyl, aryloxycarbonyl, acyloxy; alkylthio, arylthio, alkylsulfinyl, arylsulfinyl, alkylsulfonyl and arylsulfonyl radical.

4. A catalyst for the polymerization of olefins according to claim 1, said catalyst further comprising: an organic aluminum compound.

5. A catalyst for the polymerization of olefins according to claim 2, wherein Y is a substituent selected from the group consisting of a hydrogen atom, an alkyl radical having 1 to 10 carbon atoms, an aryl radical having 6 to 10 carbon atoms, an alkenyl radical having 2 to 10 carbon atoms, an alkynyl radical having 2 to 10 carbon atoms, an arylalkyl radical having 7 to 20 carbon atoms, an arylalkenyl radical having 8 to 20 carbon atoms, an alkylaryl radical having 7 to 20 carbon atoms; a silyl radical; a halogen atom, a halogenated hydrocarbon radical; cyano, nitro, nitroso, isocyanide, cyanate, isocyanate, amino, amido; alkoxy, aryloxy, acyl, alkoxycarbonyl, aryloxycarbonyl, acyloxy; alkylthio, arylthio, alkylsulfinyl, arylsulfinyl, alkylsulfonyl and arylsulfonyl radical.

6. A catalyst for the polymerization of olefins according to claim 2, said catalyst further comprising: an organic aluminum compound.

7. A catalyst for the polymerization of olefins according to claim 3, said catalyst further comprising: an organic aluminum compound.

8. A catalyst for the polymerization of olefins according to claim 5, said catalyst flitter comprising: an organic aluminum compound.

* * * * *